US008644921B2

(12) United States Patent
Wilson

(10) Patent No.: US 8,644,921 B2
(45) Date of Patent: *Feb. 4, 2014

(54) NEUROMODULATION SYSTEM AND METHOD FOR TREATING APNEA

(75) Inventor: Willard Wilson, Saint Paul, MN (US)

(73) Assignee: Neurostream Technologies G. P., Quebec (CA)

( * ) Notice: Subject to any disclaimer, the term of this patent is extended or adjusted under 35 U.S.C. 154(b) by 50 days.

This patent is subject to a terminal disclaimer.

(21) Appl. No.: 13/108,122

(22) Filed: May 16, 2011

(65) Prior Publication Data
US 2012/0253249 A1 Oct. 4, 2012

Related U.S. Application Data

(60) Provisional application No. 61/468,404, filed on Mar. 28, 2011.

(51) Int. Cl.
*A61N 1/04* (2006.01)

(52) U.S. Cl.
USPC ............... 607/2; 607/42; 607/72; 600/544; 600/546

(58) Field of Classification Search
USPC ..................... 607/2, 42, 72; 600/544, 546
See application file for complete search history.

(56) References Cited

U.S. PATENT DOCUMENTS

| 4,289,142 A | 9/1981 | Kearns |
| 5,824,027 A | 10/1998 | Hoffer et al. |
| 6,587,725 B1 | 7/2003 | Durand et al. |
| 6,681,401 B1 * | 1/2004 | Marino ............................ 2/19 |
| 6,684,101 B2 * | 1/2004 | Daum ......................... 600/547 |
| 7,282,980 B2 | 10/2007 | Baru |
| 2005/0149146 A1 * | 7/2005 | Boveja et al. .................. 607/58 |
| 2006/0189881 A1 | 8/2006 | Fassio |
| 2007/0150006 A1 * | 6/2007 | Libbus et al. .................... 607/2 |
| 2008/0065184 A1 | 3/2008 | Hoffer et al. |
| 2010/0016908 A1 * | 1/2010 | Martin et al. .................... 607/3 |
| 2010/0125310 A1 * | 5/2010 | Wilson et al. .................. 607/42 |
| 2010/0280577 A1 | 11/2010 | Roy et al. |

FOREIGN PATENT DOCUMENTS

| WO | 2008046190 A1 | 9/2007 |
| WO | 2008005903 | 1/2008 |
| WO | 2008097518 A2 | 8/2008 |

OTHER PUBLICATIONS

International Search Report dated Aug. 26, 2011 regarding PCT/US2011/36653, 17 pages.
McFarland, D.H. and Kimoff, R. J., Swallowing function and upper airway sensation in obstructive sleep apnea, J. of Applied Physiology, 2007, pp. 1587-1594, vol. 102.
Teramoto, S. et al, Impaired Swallowing Reflex in Patients With Obstructive Sleep Apnea Syndrome, Chest, 1999, pp. 17-21, vol. 116, No. 1.

(Continued)

Primary Examiner — Christopher D Koharski
Assistant Examiner — Michael Carey
(74) Attorney, Agent, or Firm — Polsinelli PC

(57) ABSTRACT

The present disclosure provides systems and methods for treating apnea by controlled delivery of a swallow stimulus to a subject in which apnea is detected. In the systems and method, burst electrical or mechanical stimulation to one or more swallow-related nerves and/or muscles can be timed for delivery between the expiratory phase of the respiration cycle, following detection of an apneic event in the subject.

67 Claims, 7 Drawing Sheets

(56) References Cited

OTHER PUBLICATIONS

Weaver, T.E. and Crunstein, R.R., Adherence to Continuous Positive Airway Pressure Therapy, Proc Am Thorac Soc, 2008, pp. 173-178, vol. 5.

Jobin, V. et al, Swallowing function and upper airway sensation in obstructive sleep apnea, J. of Applied Physiology, 2007, pp. 1587-1594, vol. 102.

Weaver, T.E. and Grunstein, R.R., Adherence to Continuous Positive Airway Pressure Therapy, Proc Am Thorac Soc, 2008, pp. 173-178, vol. 5.

International Search Report dated Apr. 21, 2009 regarding PCT/CA2008/002036, 3 pages.

Office Action mailed Nov. 9, 2011; U.S. Appl. No. 12/273,118 (6 pages).

Bevan; "Tonically Active Vagal Pulmonary Afferent Neurones"; Life Sciences, Pergamon Press, Oxford, GB; vol. 4; No. 23; Dec. 1, 1965; pp. 2289-2294.

* cited by examiner

NEUROMODULATION SYSTEM AND METHOD FOR TREATING APNEA

CROSS-REFERENCE TO RELATED APPLICATIONS

This application claims priority to U.S. Patent Application Ser. No. 61/468,404 filed Mar. 28, 2011, which is incorporated herein by reference in its entirety.

TECHNICAL FIELD

The subject invention relates to methods for treating apnea in a subject suffering or at risk of suffering from episodes of apnea or hypopnea, including obstructive sleep apnea.

BACKGROUND

Sleep apnea/hypopnea affects around 5% of the adult U.S. population. Short-term effects consist of complete (apnea) or partial (hypopnea) termination of airflow, decreased oxygen in the blood, increased $CO_2$ in the blood, interrupted sleep, and excessive daytime sleepiness. Long-term effects may include hypertension, diabetes, heart attack, stroke, arrhythmia and brain damage.

The principal forms of sleep apnea are: 1) obstructive sleep apnea (OSA), characterized by a physical blockage of the upper airway during sleep, 2) central sleep apnea (CSA), caused by a decreased central respiratory drive during sleep, and 3) mixed sleep apnea, which includes components of both OSA and CSA. OSA is the most common and dangerous of all sleep-related breathing disorders. While CSA is uncommon in its pure form, it is prevalent in patients with congestive heart failure, as a component of Cheyne-Stokes respiration.

The obstructive component in OSA is related to decreased tone in the upper airway as the muscles relax during sleep. In the flaccid airway, muscle tone is insufficient to overcome the combined forces of gravity, surrounding tissue, and the vacuum created by inspiration. Together, these forces act to reduce the cross-sectional area of the airway, decreasing or eliminating airflow.

The treatment of choice for sleep apnea is continuous positive air pressure (CPAP). Basically, CPAP maintains an open airway by inflating it with pressurized air through a nose or face mask. Used properly, CPAP is 100% effective for treating OSA. Although CSA has a neurological origin, it has also been successfully treated with positive air pressure. Despite its efficacy, however, CPAP treatment is poorly tolerated by sleep apnea patients. In one recent survey, CPAP non-compliance (less than 4 h/night) was reported in between 46% and 83% of patients (Weaver and Grunstein, 2008). Reasons for non-compliance include discomfort, claustrophobia, pressure sores, dry nose or mouth, and machine noise.

The most common alternative to CPAP is a surgical removal of the uvula, caudal soft palate, and tonsils. This procedure has a success rate of about 50%. Other surgical treatments, such as tongue reduction, advancement of the tongue, tracheostomy, or implants to stiffen the soft palate have had limited benefit relative to their invasiveness, risk, and irreversibility. Non-surgical approaches such as weight loss, medication, changes in sleeping position or dental appliances also suffer from limited effectiveness or compliance.

Certain implantable medical devices for detecting and/or treat sleep apnea are under investigation but not yet mature. These devices are similar in general design to cardiac pacemakers. With regard to detection, implantable devices have been described that detect apnea by monitoring certain biological signals indicative of respiratory activity, for example, the bioelectric activity of the diaphragm, intercostal muscles, or their efferent nerves, or the bioelectric activity of upper airway muscles or their efferent nerves. Implantable sensors of thoracic pressure and of blood oxygenation are known. With regard to treatment, implantable devices have been described that terminate apnea using drug delivery, atrial overdrive pacing or electrical stimulation of the nerves or muscles that control respiratory activities. Apnea treatments and devices involving delivery of other types of therapeutic response have not been well explored and may provide useful alternatives.

SUMMARY OF THE INVENTION

In one aspect, the present disclosure provides a system for treating apnea in a subject, comprising an electrode configured for positioning in contact with the internal branch of the superior laryngeal nerve (iSLN) of the subject; a control unit comprising a signal conditioning module for conditioning an electroneurogram signal from the electrode; an apnea monitoring and detection module operatively coupled to the signal conditioning module and configured for computing an index of respiratory activity from the conditioned electroneurogram signal, wherein when the index of respiratory activity is at or above a predetermined level, the index of respiratory activity is indicative of an occurrence of an apneic event; and a therapy control module operatively coupled to the apnea monitoring and detection module, wherein the therapy control module is configured to control delivery of a swallow stimulus to the subject when the index of respiratory activity is indicative of an occurrence of an apneic event. In the system, the swallow stimulus can be at least one of: electrical stimulation to at least one swallow-related nerve, electrical stimulation to at least one swallow-related muscle, and mechanical stimulation to at least one swallow-related sensory receptor. The swallow stimulus may include burst electrical stimulation or burst mechanical stimulation. A swallow stimulus may comprise, for example, mechanical stimulation to at least one swallow-related sensory receptor comprising delivery of a liquid to at least one of the oral, nasal, or pharyngeal cavity of the subject. The system may further comprise a stimulation module operatively coupled to the therapy control module; and a stimulation output device coupled to the stimulation module and configured for delivery of the swallow stimulus to the subject, wherein the stimulation module is configured to generate the swallow stimulus through the stimulation output device. The stimulation output device may comprise, for example, a stimulation electrode coupled to the stimulation module and configured for positioning in contact with at least one swallow-related nerve or muscle, wherein the stimulation module is configured to generate electrical stimulation through the stimulation electrode to at least one swallow-related nerve or muscle. In such a system, the therapy control module may be configured to activate bursts of electrical stimulation to at least one swallow-related nerve or muscle. Alternatively or in addition, the stimulation output device may comprise a mechanical stimulation delivery device configured for positioning adjacent to at least one swallow-related sensory receptor in the skin or mucosa of the subject, wherein the stimulation module is configured to generate mechanical stimulation through the mechanical stimulation delivery device. For example, the mechanical stimulation delivery device may comprise a device configured for delivery of a liquid to the oral, nasal, or pharyngeal cavity of the subject. In such a system, the therapy control module may be configured to activate bursts of mechanical stimulation to at least one swallow-related sensory receptor.

In any of the systems described herein, the apnea monitoring and detection module may be further configured to detect an apnea, including obstructive apnea obstructive hypopnea, central apnea, and/or central hypopnea. In any system, the index of respiratory activity can be indicative of the timing and amplitude of at least one of upper airway pressure, airway stretch, and airway temperature. In an exemplary system, the index of respiratory activity is indicative of upper airway pressure. In any system, the index of respiratory activity may be further indicative of the respiratory phase in the subject over time, wherein the respiratory phase comprises at least one of an inspiratory phase, an expiratory phase and a zero flow phase.

In a system wherein the index of respiratory activity is indicative of respiratory phase, the therapy control module may be further configured to synchronize delivery of burst mechanical stimulation, to at least one swallow-related sensory receptor in the skin or mucosa of the subject between inspiratory phases of the subject, the burst stimulation sufficient to elicit all or part of a swallow sequence in the subject. Alternatively or in addition, in a system wherein the index of respiratory activity is indicative of respiratory phase, the therapy control module may be further configured to synchronize delivery of burst electrical stimulation, to at least one swallow-related muscle between inspiratory phases of the subject, the burst stimulation sufficient to elicit all or part of a swallow sequence in the subject. Alternatively or in addition, in a system wherein the index of respiratory activity is indicative of respiratory phase, the therapy control module may be further configured to synchronize delivery of burst electrical stimulation to at least one swallow-related nerve between inspiratory phases of the subject, the burst stimulation sufficient to elicit all or part of a swallow sequence in the subject.

In any of the systems, the swallow-related nerve may be, for example, an afferent nerve or an efferent nerve. In a system configured for stimulation of an afferent nerve, the stimulation can trigger swallow reflexive pattern activity in the central nervous system of the subject that is sufficient to elicit all or part of a swallow sequence by the subject. In any system configured for stimulation of a swallow-related nerve, the swallow-related afferent nerve can be, for example, the superior laryngeal nerve (SLN), the internal branch of the superior laryngeal nerve, the glossopharyngeal nerve or the pharyngeal branch of the glossopharyngeal nerve. In a system configured for stimulation of an efferent nerve, the stimulation can elicit motor activity in at least one effector of a swallow response in the subject, the motor activity comprising all or part of a swallow sequence by the subject. In any system configured for stimulation of a swallow-related nerve, the swallow-related efferent nerve can be, for example, the recurrent laryngeal nerve, the external branch of the superior laryngeal nerve, the brancial motor branch of the glossopharyngeal nerve, the mandibular nerve, the medial pterygoid nerve, or pharyngeal branch of the vagus nerve.

In any of the systems, the apnea monitoring and detection module may be further configured to compare the index of respiratory activity following delivery of each burst of stimulation, to a predetermined recovery threshold and thereby detect recovery from apnea in response to each burst of stimulation. The therapy control module may be further configured to repeat delivery of burst stimulation when recovery from apnea is not detected. Systems not including a mechanical stimulation delivery device for delivering a liquid to the oral, nasal or pharyngeal cavity of the subject may be configured as fully implantable.

In another aspect, the present disclosure provides a method for treating apnea comprising (a) sensing a respiratory signal in a subject; (b) detecting apnea based on the respiratory signal; (c) when apnea is detected, triggering the delivery of a swallow stimulus sufficient to elicit all or part of a swallow in the subject; and optionally repeating steps (a) through (c). In the method, the respiratory signal may comprise a signal derived from a neural electrode, external sensor, or implanted sensor indicating at least one of: airway pressure, temperature, stretch, position, shear or slip, vibration, texture, touch, touch and pressure, muscle stretch, muscle "drive", air flow, blood pressure or osmolarity, blood $O_2$, $CO_2$ or pH, or any combination thereof. In the method, the swallow stimulus may comprise at least one of: electrical stimulation to at least one swallow-related nerve, electrical stimulation to at least one swallow-related muscle, and mechanical stimulation to at least one swallow-related sensory receptor in the skin or mucosa of the subject, the swallow stimulus sufficient to elicit all or part of a swallow sequence in the subject. The swallow stimulus may comprise burst electrical stimulation or burst mechanical stimulation. Mechanical stimulation may comprise stimulation to at least one swallow-related sensory receptor, comprising for example delivery of a liquid to at least one of the oral, nasal, or pharyngeal cavity of the subject. Alternatively or in addition, the swallow stimulus may comprise electrical stimulation to at least one swallow-related nerve or muscle. In a case where stimulation targets more than one swallow-related nerve, muscle and/or sensory receptor, stimulation may be delivered across the targets simultaneously or sequentially. Sequential stimulation may be used to create a more natural progression of the swallow sequence, replicating the timing, duration, and sequencing of the more than fifty individual muscles involved. In the method, the respiratory signal may further comprise a signal indicative of respiratory phase in the subject over time, wherein the respiratory phase comprises at least one of an inspiratory phase, an expiratory phase and a zero flow phase. In a method wherein the respiratory signal comprises a signal indicative of respiratory phase in the subject over time, triggering of the electrical burst stimulation or mechanical burst stimulation may comprise synchronizing the delivery of the burst stimulation between inspiratory phases of the subject. Any of the above methods may further comprise computing an index of respiratory activity indicative of at least one of upper airway pressure, airway stretch, and airway temperature. In an exemplary such method, the index of respiratory activity is indicative of upper airway pressure.

In another aspect, the present disclosure provides a method for treating sleep apnea, the method comprising (a) recording an electroneurogram signal from the internal branch of the superior laryngeal nerve (iSLN) of the subject; (b) conditioning the electroneurogram signal; (c) computing an index of respiratory activity from the conditioned electroneurogram signal; (d) reporting an occurrence of an apneic event when the index of respiratory activity is at or above a predetermined level; and (e) upon occurrence of an apneic event, triggering delivery of a swallow stimulus to the subject, wherein the swallow stimulus is sufficient to elicit all or part of a swallow sequence in the subject. In the method, the swallow stimulus may comprise at least one of: electrical stimulation to at least one swallow-related nerve, electrical stimulation to at least one swallow-related muscle, and mechanical stimulation to at least one swallow-related sensory receptor in the skin or mucosa of the subject. The swallow stimulus may comprise burst electrical stimulation or burst mechanical stimulation. For example, the swallow stimulus may comprise mechanical stimulation to at least one swallow-related sensory receptor, comprising delivery of a liquid to at least one of the oral, nasal, or pharyngeal cavity of the subject. Alternatively or in addition, the swallow stimulus may comprise electrical stimulation to at least one swallow-related nerve or muscle. The swallow stimulus may comprise electrical stimulation to at least two swallow-related nerves, at least two swallow-related muscles, or at least a swallow-related nerve and a swallow-related muscle. In a case where stimulation targets more than one swallow-related nerve, muscle and/or sensory receptor, stimulation may be delivered across the targets simultaneously or sequentially. Sequential stimulation may be used to create a more natural progression of the swallow sequences, replicating the timing, duration, and sequencing of the more than 50 individual muscles involved. In the method, the respiratory signal may further comprise a signal indicative of respiratory phase in the subject over time, wherein the respiratory phase comprises at least one of an inspiratory phase, an expiratory phase and a zero flow phase. In the method, when the respiratory signal is indicative of respiratory phase in the subject over time, triggering of the electrical burst stimulation or mechanical burst stimulation may comprise synchronizing the delivery of the burst stimulation between inspiratory phases of the subject. In the method, the index of respiratory activity can be indicative of at least one of upper airway pressure, airway stretch, and airway temperature. In an exemplary method, the index of respiratory activity is indicative of upper airway pressure. In the method, the swallow stimulus may comprise burst electrical stimulation to at least one swallow-related nerve wherein a swallow-related nerve is an afferent nerve or an efferent nerve. The burst electrical stimulation may comprise burst electrical stimulation to at least two swallow-related nerves wherein each swallow-related nerve is independently an afferent nerve or an efferent nerve. In the method, the swallow-related nerve may be an afferent nerve, wherein stimulation of the afferent nerve elicits swallow reflexive pattern activity from the central nervous system of the subject sufficient to elicit all or part of a swallow sequence in the subject. The swallow-related nerve can be, for example, the internal branch of the superior laryngeal nerve (iSLN) or the pharyngeal branch of the glossopharyngeal nerve. The swallow-related nerve can be an efferent nerve, wherein stimulation of the efferent nerve elicits motor activity in at least one effector in a swallow sequence, the motor activity comprising all or part of a swallow sequence in the subject. The swallow-related nerve can be, for example, the recurrent laryngeal nerve, the external branch of the superior laryngeal nerve, the brancial motor branch of the glossopharyngeal nerve, the mandibular nerve, the medial pterygoid nerve, or pharyngeal branch of the vagus nerve. The method may further comprise comparing the electroneurogram signal following delivery of each burst of stimulation, to a predetermined recovery threshold and thereby detecting recovery from apnea in response to each burst of stimulation. Such a method may further comprise repeating a burst of stimulation when recovery from apnea is not detected. Delivering electrical stimulation may comprise, for example, delivering a burst of stimulus pulses having a frequency of at least about 20 Hz to about 40 Hz, wherein each pulse has an amplitude of greater than about 0.1 mA and a duration of about 200 μsec.

In another aspect, the present disclosure provides a device for treating apnea in a subject, comprising an electrode configured for positioning in contact with the internal branch of the superior laryngeal nerve (iSLN) of the subject, further configured for obtaining an respiratory signal from the iSLN and for delivering electrical stimulation to the iSLN; a control unit comprising a signal conditioning module for conditioning the electroneurogram signal from the electrode, an apnea monitoring and detection module operatively coupled to the signal conditioning module and configured for computing an index of respiratory activity from the conditioned electroneurogram signal, wherein when the index of respiratory activity is at or above a predetermined level, the index of respiratory activity is indicative of an occurrence of an apneic event, and a therapy control module wherein the therapy control module is configured to control delivery of a swallow stimulus and delivery of the swallow stimulus is triggered when the index of respiratory activity is indicative of an occurrence of an apneic event. In the device, the therapy control module can be configured to control delivery of electrical stimulation through the electrode to at least one swallow-related nerve when the index of respiratory activity is indicative of an occurrence of an apneic event. The control unit may further comprise a respiratory phase module operatively coupled to the apnea monitoring and detection module and configured to determine respiratory phase from the index of respiratory activity and to generate a respiratory phase signal from the subject. The therapy control module may be further configured to activate burst stimulation of the iSLN between inspiratory phases based on the respiratory phase signal, the burst stimulation sufficient to produce all or part of a swallow sequence in the subject. In the device, the electrode and control unit can be implantable. The device may further comprise a stimulation output device configured for oral, nasal or pharyngeal delivery of a liquid to the subject and operatively coupled to the therapy control module, wherein the therapy control module is further configured to activate oral delivery of liquid to the subject when the index of respiratory activity is indicative of an occurrence of an apneic event.

In another aspect, the present disclosure provides a method for treating dysphagia comprising (a) sensing a dysphagia signal in a subject; (b) detecting dysphagia based on the dysphagia signal; (c) when dysphagia is detected, triggering the delivery of a swallow stimulus sufficient to elicit all or part of a swallow in the subject; and (d) optionally repeating steps (a)-(c). In the method, the swallow stimulus may comprise at least one of: electrical stimulation to at least one swallow-related nerve, electrical stimulation to at least one swallow-related muscle, and mechanical stimulation to at least one swallow-related sensory receptor in the skin or mucosa of the subject. The swallow stimulus may comprise burst electrical stimulation or burst mechanical stimulation. The method may further comprise sensing a respiratory signal, wherein the respiratory signal is indicative of respiratory phase, wherein the respiratory phase is least one of an inspiratory phase, an expiratory phase and a zero flow phase, and the triggering of the burst stimulation comprises synchronizing the delivery of the burst stimulation between inspiratory phases of the subject. The swallow stimulus may comprise mechanical stimulation to at least one swallow-related sensory receptor, comprising delivery of a liquid to at least one of the oral, nasal, or pharyngeal cavity of the subject. The swallow stimulus may comprise electrical stimulation to at least one swallow-related nerve or muscle.

DETAILED DESCRIPTION

Figure 1:
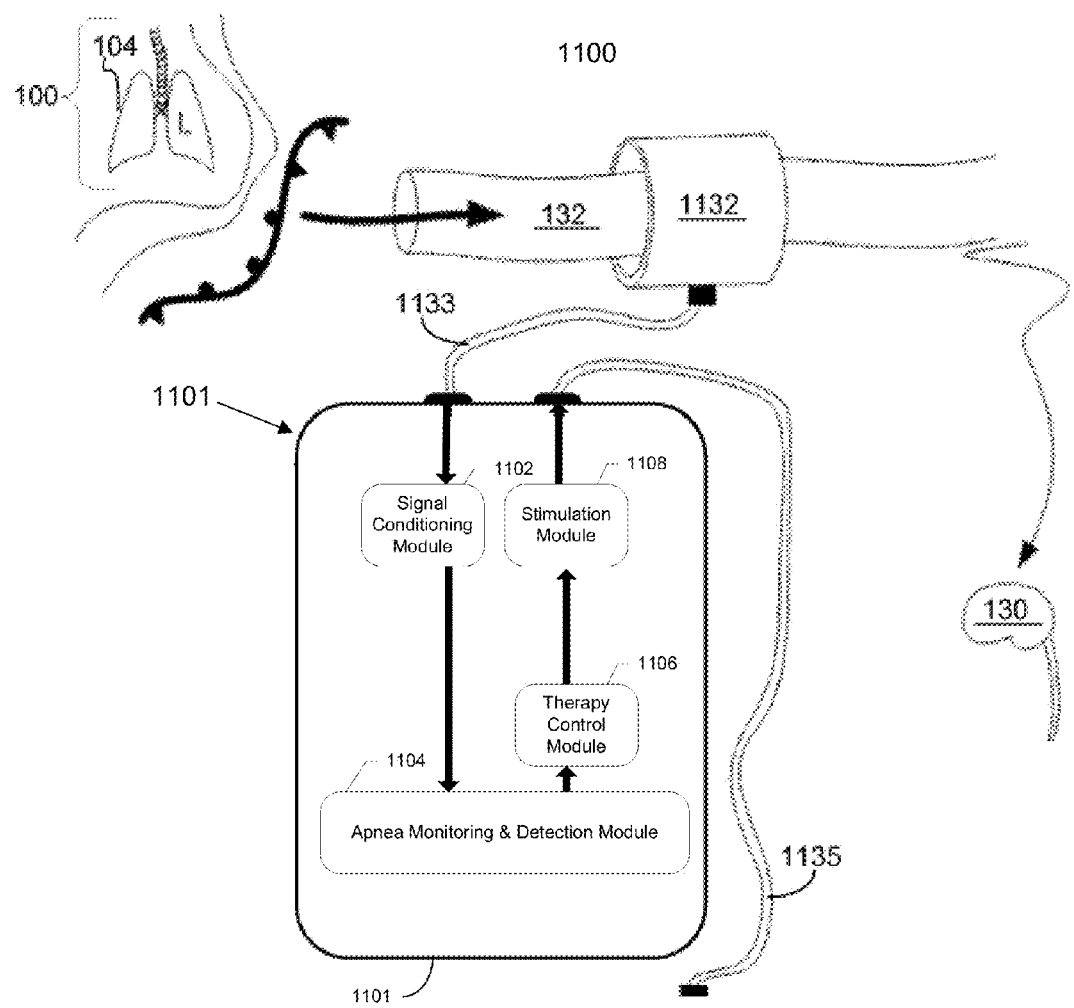
FIG. 1 is a schematic diagram of a system for treating apnea.

The present disclosure is based in part on the realization that controlled delivery of stimulation to swallow-related effectors, i.e., swallow-related nerves and/or muscles, that is effective to trigger all or part of the swallow sequence, can treat episodes of apnea in a subject that suffers from or is at risk of suffering from apnea. The method is based in part on the realization that the act of swallowing activates and repositions airway structures that are commonly involved in obstructive sleep apnea and that certain types of swallow stimulation can be used effectively to reposition airway structures, between breaths, to reestablish airway patency. In particular, the present disclosure describes for the first time the treatment of apnea by the delivery of burst electrical or burst mechanical stimulation to swallow-related nerves, swallow-related muscles, and/or swallow-related sensory receptors wherein the burst stimulation is timed for delivery between periods of inspiration. By using such timed bursts of stimulation, the disclosed processes and systems avoid the problem of inducing a counterproductive central apneic response to the stimulation, which is the frequent result of using continuous stimulation. Further, such timed bursts of stimulation are designed to elicit swallow during or just prior to expiration and to avoid swallow during or just prior to inspiration. Swallow during or prior to expiration is considered the safest respiratory phases for swallowing in adult humans and to minimize the potential for food or fluid entering the airway. Accordingly, the present disclosure provides systems, methods and devices for treating apnea in a subject. Methods for treating dysphagia are also described.

Section headings as used in this section and the entire disclosure herein are not intended to be limiting.

A. Definitions

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

The use of "or" means "and/or" unless stated otherwise. Furthermore, the use of the term "including", as well as other forms, such as "includes" and "included", is not limiting.

As used herein, unless specified otherwise, the term "apnea" encompasses any form of involuntary apnea, bradypnea or hypopnea of obstructive, central or mixed origin, including sleep apnea and sleep hypopnea, and also includes any complex episode of apnea or hypopnea occurring during sleep or wakefulness, as in Cheyne-Stokes respiration.

As used herein to describe a nerve or muscle, the term "swallow-related" refers to the nerve or a muscle as one for which normal function includes activity that effects, or contributes to effecting, all or any part of a normal oropharyngeal swallow sequence, wherein a swallow sequence refers to that reflexive and centrally programmed series of muscle movements beginning with muscle movements in an oral phase under voluntary muscular control and proceeding with pharyngeal and esophageal phases under involuntary neuromuscular control.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamster, guinea pig, cat, dog, rat, mouse, non-human primate (including but not limited to a monkey, such as a cynomolgous monkey, rhesus monkey, and chimpanzee), and a human). Preferably, the subject is a human.

Unless otherwise defined herein, scientific and technical terms used in connection with the present disclosure shall have the meanings that are commonly understood by those of ordinary skill in the art. For example, any nomenclatures used in connection with, and techniques of, neural science, electrophysiology, animal and cellular anatomy, cell and tissue culture, molecular biology, immunology, and microbiology described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

B. Systems for Treating Apnea

The present disclosure uses certain terms as used in U.S. patent application Ser. No. 12/273,118, filed May 20, 2010 (U.S. Pub. No. 2010/0125310), the entire contents of which is hereby incorporated by reference. For example, the terms "normal respiration", "apnea", "obstructive sleep apnea" (OSA), and "central sleep apnea" (CSA), as used herein, each have the same meaning as that for each term as used in U.S. Pub. No. 2010/0125310. Additionally, the detection and classification of apnea events as described herein is consistent with the detection and classification of apnea events as described in U.S. Pub. No. 2010/0125310, i.e. involves calculating an index of respiratory activity (IRA) that is indicative of the amplitude and timing of respiratory activity based on the amplitude and timing of a respiratory signal, such as an electroneurogram (ENG) signal from a nerve such as the internal branch of the superior laryngeal nerve (iSLN), or another sensor of respiratory activity as described elsewhere herein. Details for calculating an IRA that is indicative of the amplitude and timing of a respiratory signal are described in U.S. Pub. No. 2010/0125310.

A system for treating apnea in a subject as described herein can be considered a neuroprosthesis. The term "treating" encompasses detecting and identifying an apnea in a subject, and treating in the sense of delivering a therapy to the subject.

It should be understood that throughout the description, the various units, modules, sub-modules and algorithms of the system as described are readily implemented using for example one or more electronic circuits, microcontrollers or digital signal processors (DSP).

Referring to FIG. 1, a schematic diagram is shown of an exemplary neuroprosthesis 1100 for detection, identification and treatment of apnea by monitoring respiratory-related activity, interpreting these respiratory signals to detect and classify adverse events in the airway, and stimulating nerves, muscles and/or sensory receptors to elicit appropriate corrective responses to adverse respiratory events. As the system is shown in FIG. 1, apnea is detected and identified by monitoring respiratory-related activity from the internal branch of the superior laryngeal nerve (iSLN) 132. The iSLN carries afferents from receptors in the laryngeal mucosa toward the central nervous system 130. Other peripheral nerves carrying afferents modulated by respiratory condition may also be monitored, including the recurrent laryngeal nerve, the main branch of the SLN, the vagus nerve, the phrenic nerve, each nerve alone, or in combination with the other(s).

It should be understood that other approaches to detecting and identifying apnea may be taken, including monitoring the respiratory-related activity of other nerves, or monitoring other physical indicators of respiratory state, such as airway pressure, muscle activity or airway flow as described in further detail below. Detection may be achieved using any means capable of detecting a physical signal and transducing the signal to an electrical signal that can be used for analysis. Various physical indicators of respiration and respiratory state are amenable to detection and monitoring, including but not limited to airway pressure, air flow, muscle stretch, muscle position, muscle "drive", blood pressure, blood osmolarity, blood gas ($CO_2$ and $O_2$), heart rate, and blood pH. Techniques and apparatus for detecting and monitoring such physical indicators are well known and widely available and can be used alone or in combination, and are generally coupled to leads that transmit data to analytic components. For example, multiple electrodes can be placed in or on the body to measure, for example, breathing rate and heart rate. An oximeter can be used to detect and monitor blood oxygen levels in the blood. A blood pressure cuff or arterial catheter may also be used, to detect and monitor blood pressure. EMG leads can be used to detect breathing muscle activity. A manometer can be placed in the nasal cavity to detect airway pressure.

Additionally, respiratory activity may be monitored from any of a number of anatomical elements involved in respiration and control of respiration. For example, respiratory activity may also be monitored from nerves carrying efferent signals to muscles of the upper airway, diaphragm, or intercostal muscles, or by monitoring the activity of these respiratory muscles themselves, alone, or in some combination with other nerves or muscles modulated by respiratory activity. Respiratory activity may also be monitored from afferent nerves carrying signals from peripheral receptors as described below.

Referring again to FIG. 1, neuroprosthesis 1100 includes a control unit 1101 comprising a signal conditioning module 1102, an apnea monitoring and detection module 1104, a therapy control module 1106 and a stimulation module 1108, operatively coupled to one another as shown. A recording electrode 1132 is placed in, around, or near a peripheral nerve that carries afferent neural activity from receptors in the upper airway 100 toward the central nervous system 130. The nerve can be for example the iSLN 132. A lead 1133 connects the electrode 1132 to the control unit 1101 and signal conditioning module 1102. Swallow stimulation signals are routed from the stimulation module 1108 over a lead 1135 to a stimulation output device (not shown in FIG. 1), such as a swallow stimulation device configured to deliver an appropriate swallow stimulus to the target nerve and/or muscle.

It will be appreciated that multiple recording electrodes 1132 can be used, depending in the application and anatomical location being monitored, to simultaneously or sequentially monitor multiple signal sources. The recording electrode 1132 may also target other nerves carrying afferent signals from peripheral receptors that exhibit modulations of bioelectric potential correlated with respiration. Receptors that may be monitored to determine respiratory condition include: mechanoreceptors sensitive to negative airway pressure, positive airway pressure, stretch, position, shear or slip, vibration, texture, touch, touch and pressure, muscle stretch, muscle "drive", air flow, blood pressure or osmolarity; chemoreceptors sensitive to $CO_2$, $O_2$, or pH; thermoreceptors sensitive to temperature or airflow; nociceptors sensitive to polymodal pain, or some combination of the above. An exemplary system includes at least one electrode 1132 sensitive to at least one of upper airway pressure, airway stretch, and airway temperature or multiple electrodes sensitive to a combination thereof.

The signal conditioning module 1102 conditions the iSLN ENG signal, for example amplifying it, recorded by the first electrode 1132 and provides the conditioned iSLN ENG signal to the apnea monitoring and detection module 1104, which includes an algorithm that uses the conditioned iSLN ENG signal to monitor respiratory activity, detect apnea events before they result in arousal from sleep and identify the type and severity of apnea event. The signal conditioning module 1102 may include, without limitation, a signal amplifier and a rectifier circuit. Examples of amplifiers and rectifier circuits that may be used are respectively disclosed in U.S. Patent Application Publication No. 2006/0189881 entitled "IMPLANTABLE SIGNAL AMPLIFYING CIRCUIT FOR ELECTRONEUROGRAPHIC RECORDING", published Aug. 24, 2006, by Baru Fassio and U.S. Pat. No. 7,282,980 entitled "PRECISION RECTIFIER CIRCUIT FOR HIGH-DENSITY, LOW-POWER IMPLANTABLE MEDICAL DEVICE", issued Oct. 16, 2007, to Baru Fassio.

The apnea monitoring and detection module 1104 provides information about the respiratory activity of the subject, reports sleep apnea events and/or allows remote modification of various criteria/thresholds through a communication link such as, for example, a radio frequency (RF) or infrared (IR) link (not shown). Additionally, the therapy control module 1106 may optionally allow remote selection and/or modification of the stimulation strategies and stimulation parameters through a communication link such as, for example, a radio frequency (RF) or infrared (IR) link (not shown).

The therapy control module 1106 processes input from the apnea detection and monitoring module 1104 and determines a stimulation strategy for stimulating a swallow. Output from the therapy control module 1106 to the stimulation module 1108 instructs stimulation module 1108 as to the stimulation signal to generate. The stimulation signal(s) used will depend on, e.g., whether the swallow stimulus is to be electrical or mechanical, single or multiple, etc. Signal pulses may be square pulses or arbitrary waveforms, constant voltage or constant current. Preferably, the signals are configured to generate a burst of electrical or a burst of mechanical stimulation, as described in further detail below. Stimulation location, amplitude, and/or waveform may be adjusted in a closed-loop based on current apnea/respiratory conditions relayed by apnea monitoring and detection module 1104 in response to previous stimulation. Stimulation waveforms may also contain features allowing for selective stimulation using current steering, directionally selective stimulation of efferent or afferent fibers, selectivity for stimulating axons of a particular diameter, or features designed to block transmission of undesired bioelectric activity.

The therapy control module 1106 is configured to generate a signal to the stimulation module 1108 to deliver a burst of electrical stimulation to a swallow-related nerve or muscle, wherein a burst is understood to be any series of stimulus pulses delivered at a frequency of between about 20 Hz to about 40 Hz, with a pulse amplitude of greater than about 0.1 mA, a pulse duration of about 200 µsec, and a total burst duration of between about 200 µsec to about 3 seconds; or to deliver a burst of mechanical stimulation to a swallow-related mechanoreceptor in the skin or mucosa of the subject, wherein a burst is understood to be any series of one or more mechanical stimuli with a total burst duration of between about 200 µsec to about 3 seconds.

The therapy control module 1106 may optionally allow remote selection and/or modification of the stimulation strategies and stimulation parameters through wireless a communication link such as, for example, a radio frequency (RF) or infrared (IR) link (not shown). Neuroprosthesis 1100 may include an internal power supply (not shown) or use a transcutaneous energy transfer system (not shown).

Figure 2:
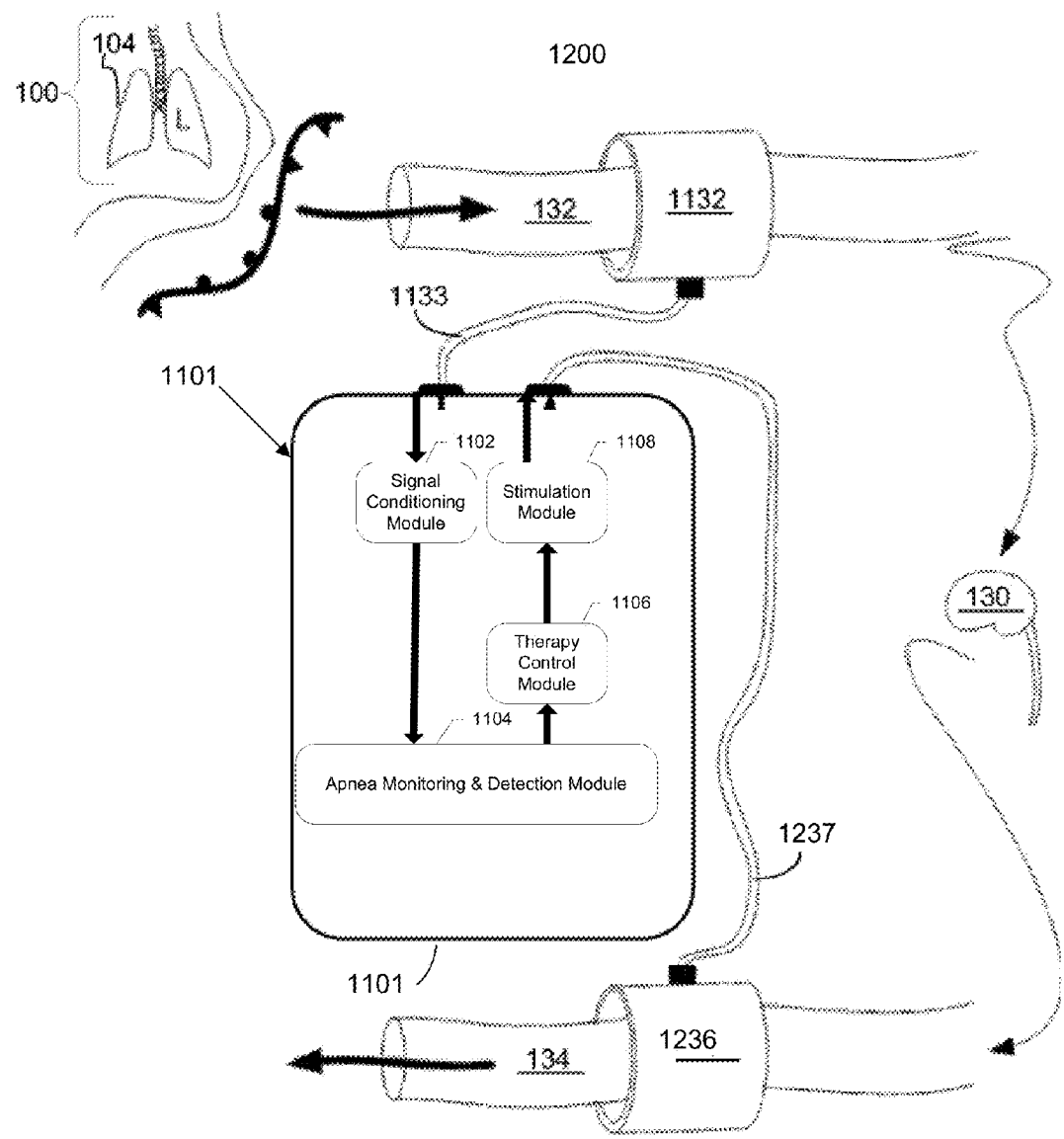
FIG. 2 is a schematic diagram of a system for treating apnea including an electrode as a stimulus output device.

Referring to FIG. 2, a schematic diagram of a neuroprosthesis 1200 is shown, in which the stimulation output device is an electrode 1236 operatively coupled to stimulation module 1108 via a lead 1237. The stimulation electrode 1236 is placed in, around or near a peripheral nerve 134 that carries afferent and/or efferent neural activity. (Peripheral nerve 134 carries efferent activity as indicated by the direction of the arrow in FIG. 2, but it should be understood that peripheral nerve 134 may carry afferent activity instead of, or in addition to efferent activity). Depending on the choice of stimulation output device, an alternative system may include a therapy output module (not shown) combining the stimulation module 1108 and stimulation output device 1236 in a single module.

In any of the systems described herein, the stimulation output device is configured to generate one or more stimuli that target at least one swallow-related nerve or muscle, or swallow-related receptor, to elicit all or part of the reflexive and pre-programmed coordinated activity of a swallow. The stimulus target may be an afferent nerve or an efferent nerve, and may include at least two swallow-related nerves wherein each swallow-related nerve is independently an afferent nerve or an efferent nerve. An afferent target is selected based on the ability of the afferent nerve, when stimulated, to elicit all or part of reflexive swallow pattern activity from the central nervous system of the subject. The target nerve can be, for example, the internal branch of the superior laryngeal nerve (iSLN), or the pharyngeal branch of the glossopharyngeal nerve. Alternatively or in addition, the swallow-related nerve can be an efferent nerve. An efferent target is selected based on the ability of the efferent nerve, when stimulated, to elicit motor activity in at least one effector in a swallow sequence, the motor activity comprising all or part of a swallow sequence in the subject. The target nerve can be, for example, the recurrent laryngeal nerve, the external branch of the superior laryngeal nerve, the brancial motor branch of the glossopharyngeal nerve, the mandibular nerve, the medial pterygoid nerve, or pharyngeal branch of the vagus nerve.

Referring again to FIG. 2, in neuroprosthesis 1200 the stimulation module 1108 is configured to generate a signal to generate an electrical swallow stimulus delivered via the electrode 1236. An electrical swallow stimulus may comprise electrical stimulation to at least one swallow-related nerve or at least one swallow-related muscle, provided that the stimulation is sufficient to elicit all or part of a swallow sequence in the subject. Delivery of the stimulus entails the process of generating a stimulus signal conditioned on the calculation of an IRA that is indicative of apnea, as described in further detail below. A swallow stimulus may therefore, alternatively or in addition to, comprise mechanical stimulation to at least one swallow-related sensory receptor, such as a mechanoreceptor, in the skin or mucosa of the subject.

Figure 3:
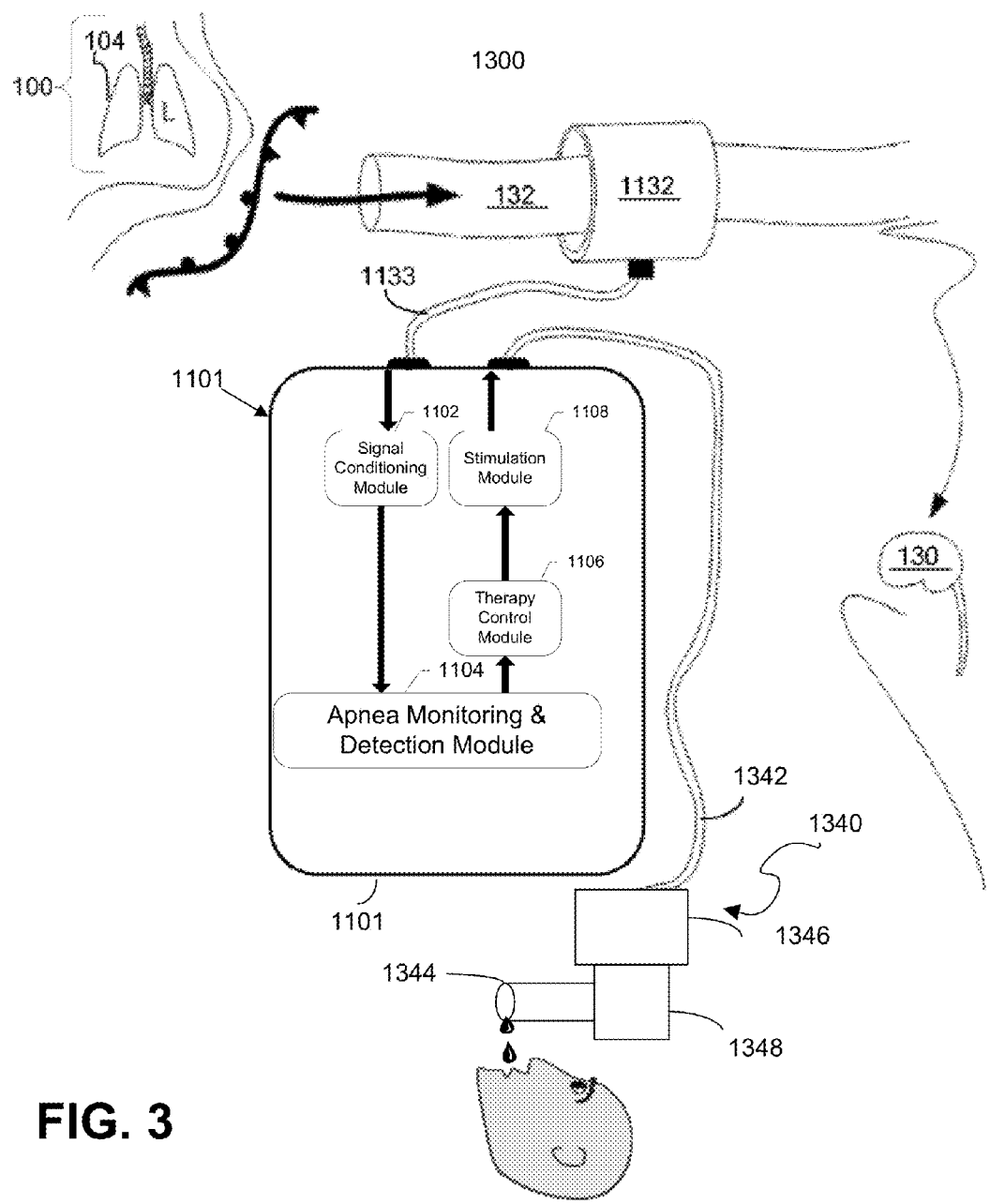
FIG. 3 is a schematic diagram of a system for treating apnea including a liquid delivery device as the stimulus output device.

Referring to FIG. 3, a neuroprosthesis 1300 includes a stimulation output device 1340 configured for oral, nasal or pharyngeal delivery of a mechanical stimulus to the subject. In system 1300, the mechanical stimulation entails delivery of an amount of a liquid of relatively low viscosity such as water or saline, to the oral, nasal, or pharyngeal cavity of the subject. The amount of liquid may be delivered as a continuous flow, or may delivered as a small discrete bolus, for example about 0.1 ml up to about 10 ml, preferably about 0.5 ml to about 2 ml, delivered as short a burst with an overall duration between about 200 µsec to about 3 seconds. For example, the mechanical stimulus may comprise a continuous delivery of a liquid at a flow rate of about 1 ml/minute over the course of the entire night. Alternatively, the liquid may be delivered as discrete bursts of liquid, as described further below. Neuroprosthesis 1300 as shown in FIG. 3 comprises a stimulation output device, configured as a liquid delivery device 1340. The liquid delivery device 1340 is operatively coupled to the stimulation module 1108 via a lead 1342 or wireless communication (not shown), and the stimulation module 1108 configured to generate the mechanical swallow stimulus through the liquid delivery device 1340. Although many possibilities for a liquid delivery device 1340 will be recognized, it may comprise, for example, a gravity-fed spout 1344 or tube coupled to a liquid reservoir 1346 via a solenoid valve 1348 configured to open and close in response to electrical signals from the stimulation module 1108. It should be understood that any device or apparatus can be used for liquid delivery device 1340, provided that it is capable of containing or providing a volume of liquid of at least about 0.5 ml, and includes an element such as the solenoid valve 1348 that can control the timing and volume of liquid delivery to the subject and can be operatively coupled to the stimulation module 1108.

Figure 4:
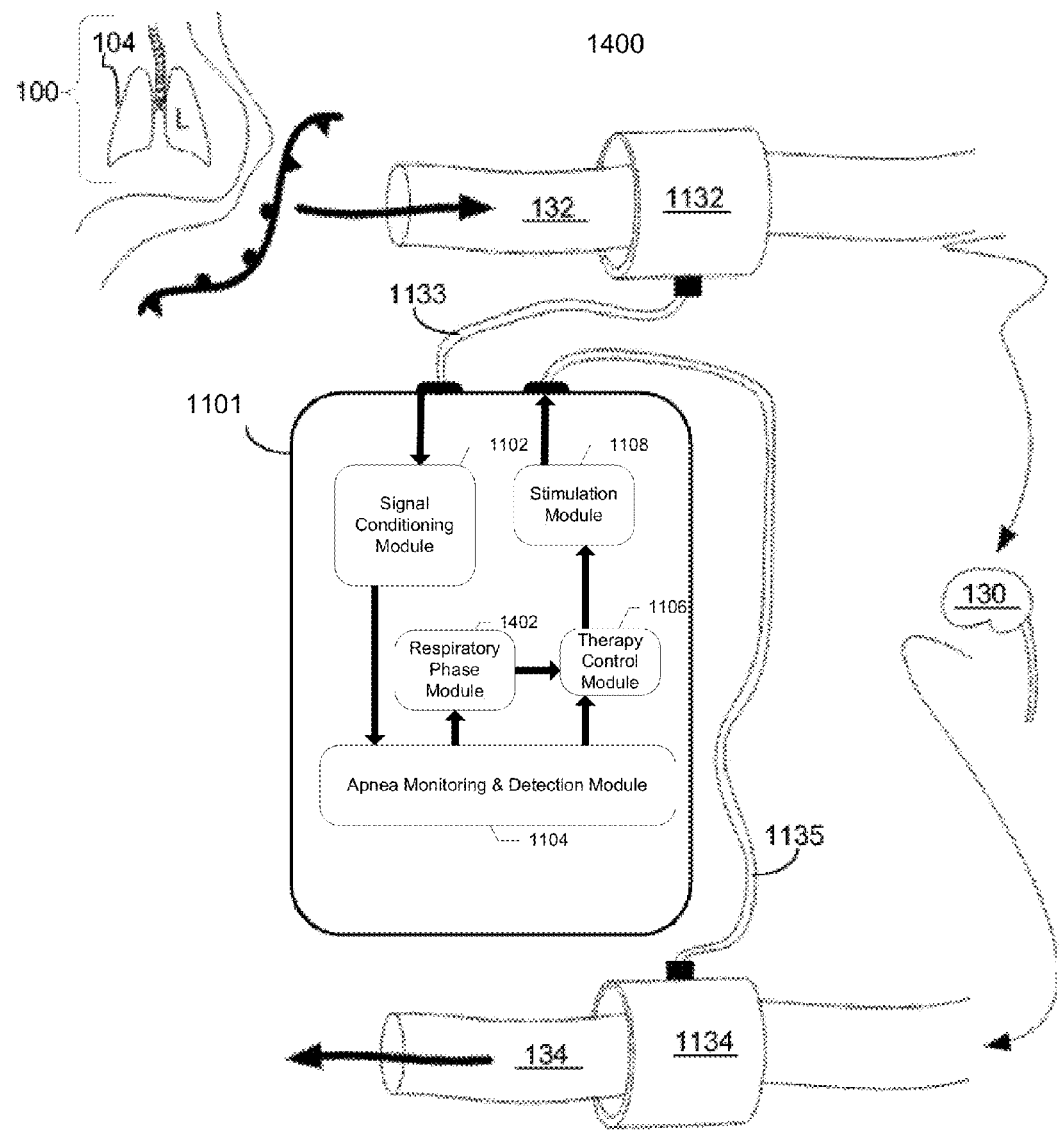
FIG. 4 is a schematic diagram a system for treating apnea including a respiratory phase module.

An exemplary neuroprosthesis 1400 as shown in FIG. 4, includes control unit 1101 further including a respiratory phase module 1402 operatively coupled to apnea monitoring and detection module 1104, which determines a respiratory phase of the subject, and provides a signal indicative of respiratory phase of the subject. Respiratory phase may include either an inspiratory phase, expiratory phase, or zero flow phase between inspiratory phase, and expiratory phases. Phase can be defined for example with reference to peak amplitude in the IRA during each breath, as determined based on a calibration of normal respiration of a given subject using, for example, polysomnographic techniques. In neuroprosthesis 1400, the therapy control module 1106 is further configured to generate a signal for delivery of a burst of stimulation to a swallow-related nerve or muscle, wherein the stimulation may be electrical or mechanical. A burst of stimulation is understood to be one (a single) pulse, or multiple stimulus pulses, wherein the single or multiple pulses together have a minimum duration of about 100-200 µsec, and a maximum duration of about 3 seconds, or about the maximum duration of an inter-breath interval. Amplitude of any stimulus pulse may vary depending on the type of stimulus being used and sensitivity of the individual subject as previously determined. For example, a burst comprising a single pulse of electrical stimulation may have a total duration of about 100-200 μsec. A burst comprising multiple electrical pulses may have a total duration of about 500 μsec to about 3 seconds. A burst comprising multiple electrical pulses may include 3, 5, 10, 20, 30, 40, 50, 60, 70, 80, 90, 100 or more individual electrical pulses. A burst of mechanical stimulation to a mechanoreceptor in the skin or mucosa of the subject, can be one (a single) pulse, or multiple stimulus pulses. It will be understood that the minimum achievable duration of each single mechanical pulse will be longer than the minimum achievable duration of each single electrical pulse due to physical limitations inherent in actuating mechanical stimulus delivery. An exemplary burst of mechanical stimulation is one comprised of a single stimulus pulse lasting about 0.5 seconds, the burst having a total duration of about 0.5 seconds. A burst comprised of multiple mechanical stimuli may have a total duration of between about 0.5 and 3 seconds, or up to about the maximum the duration of an inter-breath interval in the subject.

In neuroprosthesis 1400, the therapy control module 1106 is configured to receive the output signal of the respiratory phase module 1402 that includes a signal indicative of respiratory phase, and to generate the signal to the stimulation module 1108 to generate the stimulus burst such that delivery of the stimulus is timed to coincide with the occurrence of expiration or zero flow phase, i.e. between and not during inspiratory phases. The stimulation module 1108 may include, for example and without limitation, a pulse generator for providing current and/or voltage stimulation signals to muscles, nerves or tissue. Examples of pulse generators that may be used but are not limited to those described in U.S. patent application Ser. No. 11/920,814 entitled "IMPLANTABLE PULSE GENERATOR", filed on Oct. 9, 2007, by Roy et al.

Any system may be further configured to control, or to control and deliver a swallow stimulus to multiple targets. Selection of targets for stimulation may vary depending on the identified apneic event and the type (mechanical, electrical or combination thereof) of stimulation used. The system may be configured for example with a single electrode that is used as both a recording 1132 and stimulation 1236 electrode, for example when the iSLN is used for both recording and stimulation. Furthermore, multiple electrodes may be used, some or all of them being used both as recording 1132 and stimulation 1236 electrodes while others are used only as recording 1132 or stimulation 1236 electrodes.

The electrodes 1132 and 1236 may be, for example, cuff electrodes such as, but limited to, that described in U.S. Pat. No. 5,824,027. Other types of electrodes, leads, probes, cuff-electrodes, etc., may be used as well. Other examples of cuff electrodes that may be used are disclosed in U.S. Patent Application Publication No. 2008/0065184 entitled "NERVE CUFF, METHOD AND APPARATUS FOR MANUFACTURING SAME", published Mar. 13, 2008, by Hoffer et al. and PCT Patent Application Publication No. WO 2008/025155 entitled "NERVE CUFF INJECTION MOLD AND METHOD OF MAKING A NERVE CUFF", filed Aug. 29, 2007, by Imbeau et al.

The algorithm executed by the apnea monitoring and detection module 1104 implements steps in the processes as discussed in further detail herein below. Upon the detection of an apnea event, the apnea monitoring and detection module 1104 sends a trigger to the therapy control module 1106 along with an identification of the type of apnea event, i.e. obstructive, central, or mixed; and apnea or hypopnea, depending on the implemented algorithm, which generates a stimulus appropriate for the type of apnea event. Optionally, the apnea monitoring and detection module 1104 may also send an indication of the severity level of the apnea event, as well as timing information of previous or continuing respiration patterns, to the therapy control module 1106.

It should be understood that any of the neuroprostheses can employ wireless communication links to transmit data between and among any of the component modules, particularly from any detecting element such as electrode 1132 to signal conditioning module 1102, and/or from therapy control module 1106 to stimulation module 1108, and/or from stimulation module 1108 to a stimulation output device such as electrode 1134. For example, in an alternative embodiment of neuroprosthesis 1300 as shown in FIG. 3, iSLN ENG signals may be passed from electrode 1132 to the signal conditioning module 1102 wirelessly. Similarly, the stimulation signals from the therapy control module 1106 may be passed to the liquid delivery device 1340 wirelessly. Any neuroprosthesis described herein may further include an internal power supply (not shown) or use a transcutaneous energy transfer system (not shown). It will be further appreciated that miniature or subminiature components can be used for neuroprosthesis 1100 such that the overall small size of the device is suitable for partial or full subcutaneous implantation in a subject. A neuroprosthesis can be made fully or partially implantable, for example, when configured using miniature or subminiature components and/or wireless communication links to any components that are not implantable due to size or other factors.

C. Methods

Figure 5:
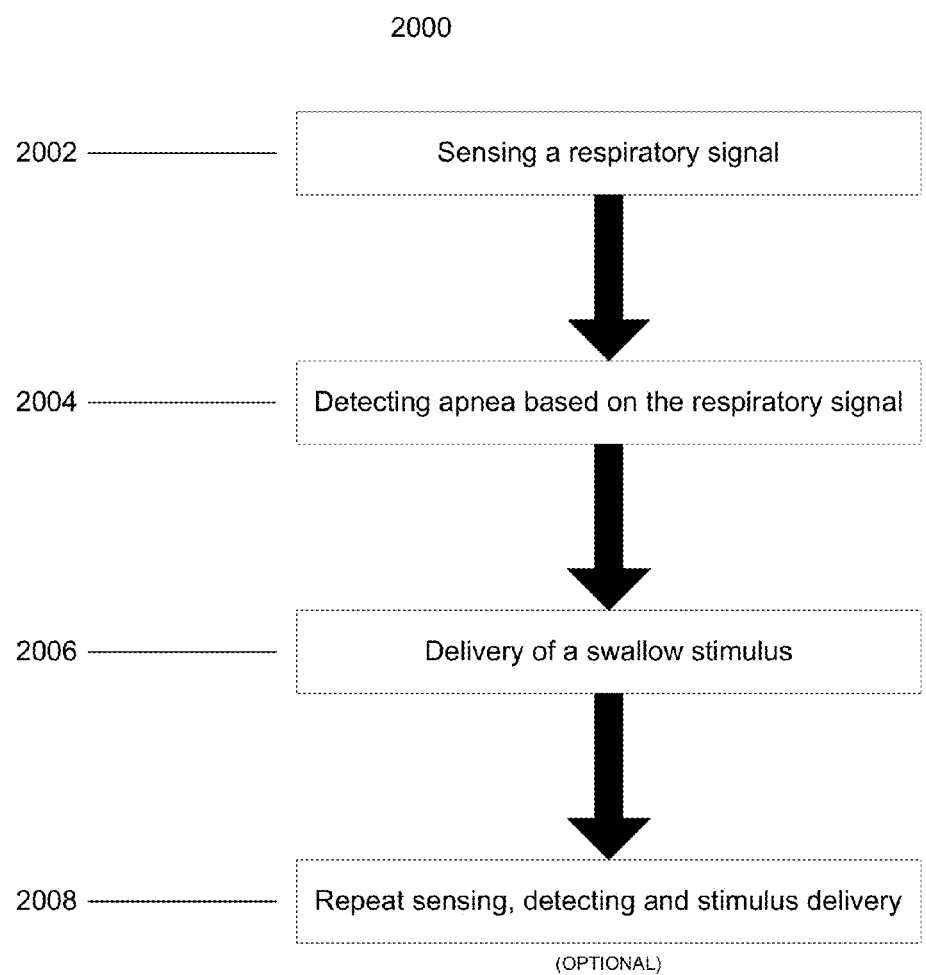
FIG. 5 is a flow diagram of a basic process for treating apnea by delivery of a swallow stimulus.

The methods encompass methods for treating apnea in a subject, and methods for treating dysphagia in a subject. Any of the neuroprostheses can be configured to implement the various methods provided. As shown in the flow diagram of FIG. 5, a process 2000 for treating apnea may comprise, for example, (a) sensing a respiratory signal in a subject 2002; (b) detecting apnea based on the respiratory signal 2004; (c) when apnea is detected, triggering the delivery of a swallow stimulus sufficient to elicit all or part of a swallow in the subject 2006; and (d) optionally repeating steps (a) through (c) 2008. Steps (a) and (b) are as described herein above and in U.S. Pub. No. 2010/0125310, the entire disclosure of which is incorporated herein. A process (not shown) for treating dysphagia may comprise, for example, a) sensing a dysphagia signal in a subject; b) detecting dysphagia based on the dysphagia signal; c) when dysphagia is detected, triggering the delivery of a swallow stimulus sufficient to elicit all or part of a swallow in the subject; and d) optionally repeating steps (a)-(c).

Briefly, as described in detail in U.S. Pub. No. 2010/0125310, during normal inspiration, the diaphragm and intercostal muscles contract, creating a negative pressure in the airway and drawing air into the lungs. Expiration, which is typically passive, results from relaxation of the diaphragm and intercostal muscles back to resting position, and elastic recoil of the lungs. The amount of air flow produced by changing airway pressure is influenced by resistance from the structures of the upper airway, including the soft palate, tongue, pharynx, and epiglottis. Airway pressure at the larynx is transduced by mucosal mechanoreceptors that are sensitive to pressure and is communicated to the central nervous system via the internal branch of the superior laryngeal nerve (iSLN).

During an obstructive sleep apnea (OSA) event, a lack of muscle tone in the upper airway allows pharyngeal structures to partially or completely block the lumen of the airway, particularly when subjects sleep on their back. Respiratory drive continues during the OSA event, the diaphragm and intercostal muscles contract, which creates a negative pressure in the airway and acts to further draw flaccid pharyngeal structures into the airway lumen. An increase in the amplitude of airway pressure is typically observed, reflecting continuing attempts on the part of the subject to breathe after airway obstruction, generating greater than normal airway pressures. The outset of the OSA event can then be identified by the sudden increase in amplitude of the inspiration and/or expiration peaks of the airway pressure.

During a central sleep apnea (CSA) event, the upper airway remains open, but diminished central respiratory drive reduces or eliminates diaphragm movement, and thus air flow during the CSA event. Despite a patent upper airway, upper airway pressure is not fully modulated after the onset of the CSA event and diminution of diaphragm movement. The outset of the CSA event can then be identified by a sudden drop in the amplitude of the inspiration and/or expiration peaks of the airway pressure.

Among other possibilities for detecting pressure in the upper airway, the electroneurogram (ENG) of the iSLN is correlated with pressure in the upper airway. An index of respiratory activity (IRA) can be calculated, which is indicative of the amplitude and timing of the ENG signal. For example, the IRA may be calculated by applying a rectification and bin-integration (RBI) algorithm to the amplified iSLN signal. The amplitude of peaks in the IRA during each breath occurs within a normal range of amplitudes which may be determined using a calibration process during normal respiration of a given subject using, for example, polysomnographic techniques. This range of amplitudes can be used to set upper and lower thresholds for apnea event detection. Peaks outside of this normal range can be detected using simple fixed-level thresholds and defined as apneic events. The upper and lower thresholds can further be used to classify, in real-time, a detected apneic event as being either an OSA event or a CSA event.

It is to be understood that although the above the IRA is calculated by applying a rectification and bin-integration (RBI) algorithm to the amplified iSLN signal, other signal processing algorithms may also be applied to calculate the IRA including: high pass filter, low pass filter, bandpass filter, notch filter, FIR filter, IIR filter, smoothing, moving average, Wiener (optimal) filter, rectification, bin-integration, multi-channel noise reduction, principal components analysis, independent components analysis, wavelet analysis, Fourier transformation, matched filtering, variance/variance ratio calculations, or some combination of the above. The raw iSLN ENG waveform may also be used directly. IRAs based on neural network analyses, cluster analysis in multidimensional feature space, cluster cutting using k-means, Bayesian expectation-maximization, closest centers, or manual cluster cutting methods may also be used.

It is to be also understood that an IRA could be computed from any number of other iSLN ENG signal features that vary with respiratory state such as event or waveform timing, interval, amplitude, duration, rise time, fall time, slope, presence, absence, pattern, 1st derivative, 2nd derivative, 3rd derivative, root mean square amplitude, peak-to-peak amplitude, variance, statistical probability or probability relative to baseline or running average.

It is also to be understood that the IRA may be calculated from other signal sources modulated by respiratory activity, including other nerves or peripheral receptors that exhibit modulations of bioelectric potential correlated with respiration or other man-made sensors that transduce respiratory-related signals. Respiratory-related variables that may be monitored to compute the IRA include: negative airway pressure, positive airway pressure, stretch, position, shear or slip, vibration, texture, touch, touch and pressure, muscle stretch, muscle "drive", air flow, blood pressure, blood osmolarity, blood $CO_2$, $O_2$, or pH, airway temperature or airflow, polymodal pain, or some combination of the above.

It is also to be understood that detection of respiratory events in the IRA using methods other than fixed-level thresholding may be used, for example noise-tracking or other adaptive thresholds, energy or non-linear energy thresholds, or any variety of other detection operations on the raw or processed data.

As described in detail in U.S. Pub. No. 2010/0125310, the outset of an OSA event or a CSA event may be identified by features of the IRA, for example with reference to an upper and a lower threshold as described above. For example, the first instance of a crossing of the upper threshold by inspiration related peaks of the IRA can be used as a criterion for identifying the outset of an OSA event. Alternatively, the peak durations of the RBI ENG may be used to identify the outset of an OSA event by setting an appropriate threshold. For a CSA event, the outset of the CSA event can be identified, for example, by noting the first absence of crossing of the lower threshold by inspiration related peaks, in a set time period. This period of time may be set, for example, to represent the average time between one or more respiration cycles. It should be understood that for both OSA and CSA events, other IRAs may be calculated in order to identify the outset of such an event. For example, peak durations and interpeak intervals of the RBI ENG can be used, by setting appropriate levels and thresholds. It is to be understood that the absence of measurements at a specified level may indicate a CSA event.

Additionally, apnea event severity can be determined from the IRA. For example, severity of the apnea event may be determined by comparing the amplitude of the apneic IRA to that observed during normal breathing. More severe apnea is characterized by IRA peaks having amplitudes far from the upper and lower thresholds, while less severe apnea or hypopnea is characterized by IRA peaks having amplitudes just above or below the upper and lower thresholds. The level of apnea thus determined can be used to adjust the parameters and characteristics of the applied neurostimulation treatment. This may include changing the stimulation waveform, increasing or decreasing the stimulus amplitude, increasing or decreasing the number of stimuli delivered, selecting electrodes in specific locations or changing the number of stimulation electrodes used. Severity levels may be assigned predetermined thresholds. It is to be understood that the number of OSA and CSA severity levels may vary depending on the precision of the circuitry and/or algorithm used.

Apneic events may be further identified as hypopnea events, i.e. OSA events can be distinguished from obstructive sleep hypopnea (OSH) events, and CSA events can be distinguished from central sleep hypopnea (CSH) events with reference to the IRA. For example, an IRA value between a first upper threshold and a second upper threshold, wherein the second upper threshold is higher than the first upper threshold, may be associated with OSH, while an IRA value greater than the second upper threshold, may be associated with OSA. Accordingly, IRA peaks between the two upper thresholds can be identified as OSH while IRA peaks above the second, higher upper threshold can be identified as OSA. Conversely, an IRA value between a first lower threshold and a second lower threshold, wherein the second lower threshold is lower than the first lower threshold, may be associated with CSH, while an IRA value lower than the second lower threshold may be associated with OSA. The range of values for which IRA peaks are defined as OSH as opposed to OSA, as well as CSH as opposed to CSA, may be determined using a calibration process during abnormal respiration of a given subject using, for example, polysomnographic techniques.

It is to be understood that OSH, OSA, CSH and CSA may be subdivided into multiple severity levels depending on the precision of the circuitry and/or algorithm used.

As described above for the OSA and CSA event detection, the variation in IRAs calculated using algorithms other than RBI ENG may also be used to determine the severity of the apneic or hypopneic event.

Apneic events may be further identified by the location(s) of the airway obstruction using, for example, the temporal profile of the IRA activity pattern acquired from a single electrode or sensor. Alternatively, or in addition, an apneic event may be further identified by the location(s) of the airway obstruction using, for example, the temporal pattern of IRA activity acquired across multiple electrodes or sensors, indicating, for example, the instantaneous pressure at multiple locations in the upper airway.

Although peaks in the IRA coincident with negative pressure receptor activity are described above, it is to be understood that receptors sensitive to other stimuli and modalities, respiratory events, phases or features, and with afferents carried by other nerves may also used. This is meant to include mechanoreceptors sensitive to positive airway pressure, stretch, position, shear or slip, vibration, texture, touch, touch and pressure, muscle stretch, muscle "drive", air flow, blood pressure or osmolarity; chemoreceptors sensitive to $CO_2$, $O_2$, or pH; thermoreceptors sensitive to temperature or airflow; nociceptors sensitive to polymodal pain, or some combination of the above.

For example, sensing a respiratory signal in a subject 2002 may comprise recording an iSLN ENG signal. Detecting apnea based on the respiratory signal 2004 includes conditioning the iSLN ENG signal, computing an IRA therefrom, and comparing the IRA to predetermined apnea criteria as described above. Delivery of a swallow stimulus is triggered 2006 when the IRA meets the predetermined apnea criteria. Detecting apnea based on the respiratory signal 2004 by computing an IRA can involve computing an IRA indicative of any one or more inputs, for example at least one of upper airway pressure, airway stretch, and airway temperature at any one or more location(s) throughout the airway. In an exemplary method, the IRA is indicative of upper airway pressure in the larynx. It should be understood that the process may involve continuous performance of steps (a) and (b) followed by performance of step (c) conditioned on the detection of apnea (or of dysphagia as described below).

Figure 6:
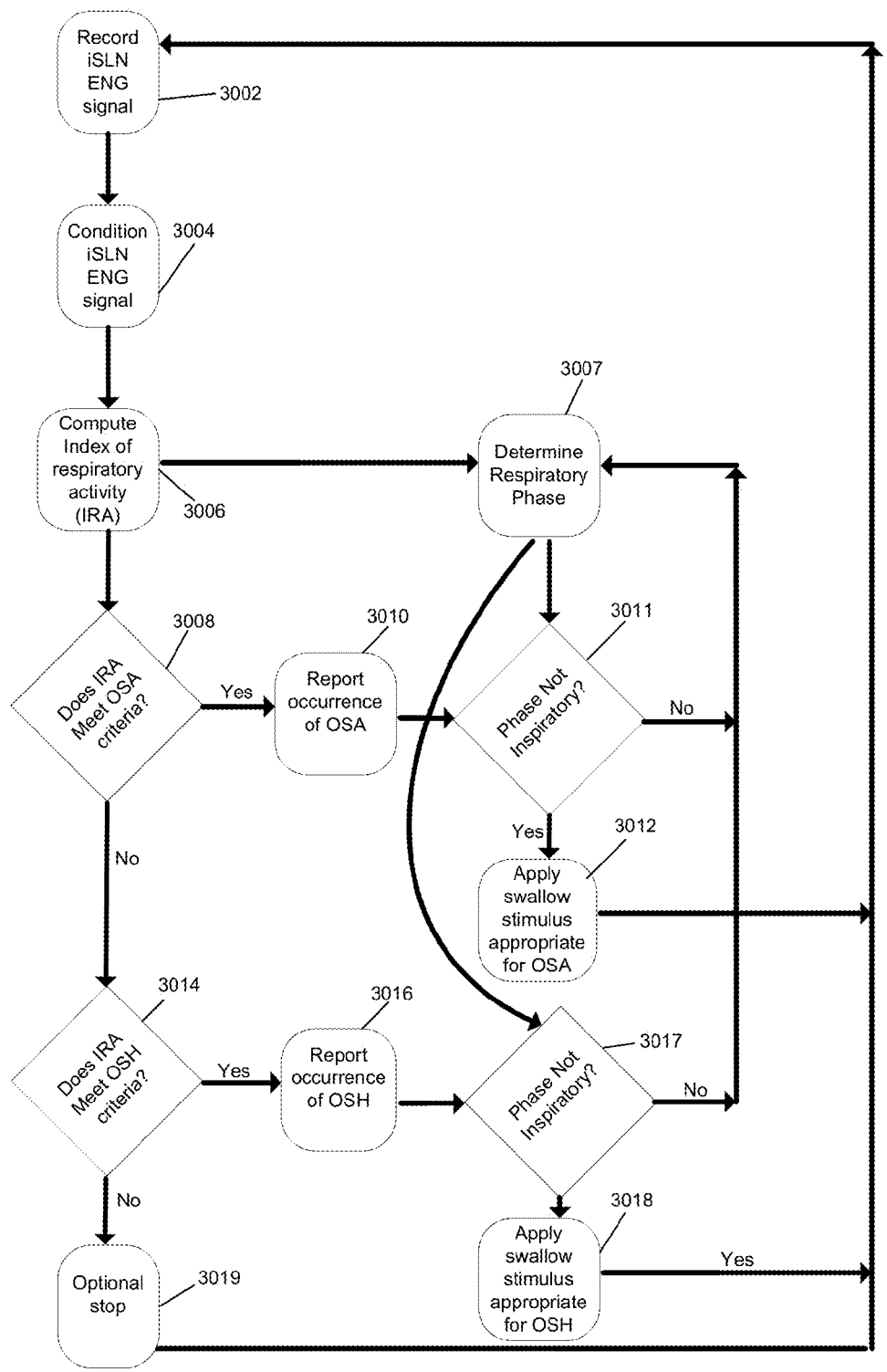
FIG. 6 is a flow diagram of a first exemplary process for treating apnea using delivery of burst stimulation.
Figure 7:
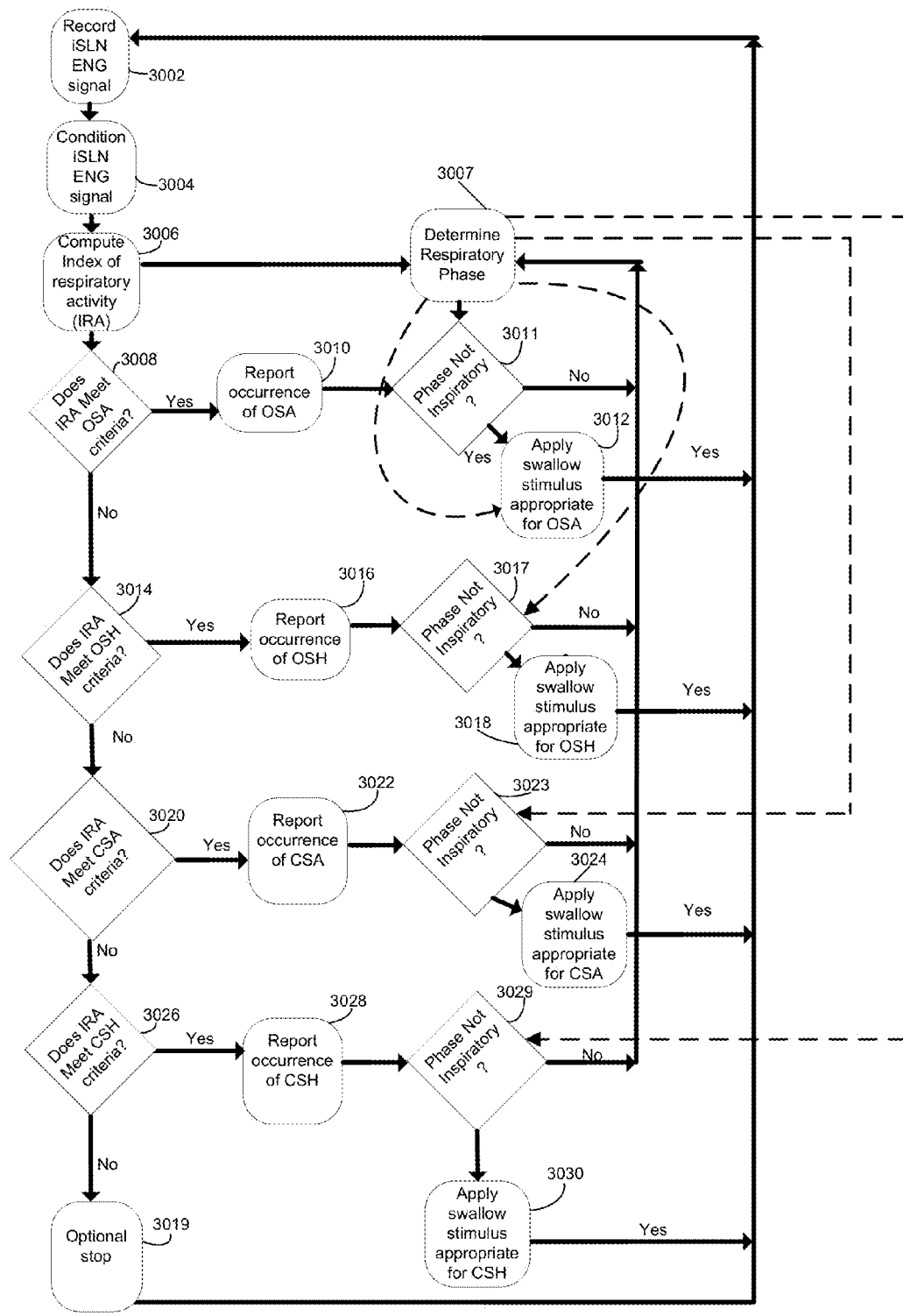
FIG. 7 is a flow diagram of a second exemplary process for treating apnea using delivery of burst stimulation.

Another exemplary process involves application of bursts of electrical or mechanical stimulation as the swallow stimulus, and further involves a timing requirement such that the delivery of the burst stimulation is timed to coincide with the expiratory phase or zero flow phase of respiration in the subject. The result is that the stimulus burst is delivered between inspiratory phases of the subject. This method is advantageous in constraining elicited swallow to respiratory phases considered safest for swallow in adult human subjects, and also to avoid undesirable side effects of iSLN stimulation, including central apnea. Exemplary such processes are shown in FIGS. 6 and 7. An exemplary process 3000 is described in the flow diagram of FIG. 6. For example, the control unit 1101 in any system as described above can implement the various steps disclosed in the blocks of process 3000 (or the exemplary process as shown in FIG. 7).

As shown in FIG. 6, process 3000 includes recording an iSLN signal 3002, conditioning the iSLN signal 3004, computing an IRA 3006, and determining a respiratory phase signal 3007. In block 3008 the IRA is further processed to determine whether OSA criteria are met. If so, an occurrence of OSA is reported in block 3010 and the process continues to block 3011. If the subject is between inspiratory phases 3011, this triggers application of an OSA-specific swallow stimulus 3012 and control returns to block 3002. If the subject is not between inspiratory phases 3011, control returns to block 3007 and phase is reevaluated in block 3011, with this process continuing until the condition is met. If OSA criteria are not met in block 3008, then the output of 3008 is null and then the IRA is evaluated to determine whether OSH criteria are met 3014. If so, an occurrence of OSH is reported 3016, and inspiratory phase is evaluated 3017. If phase is not inspiratory, an OSH specific swallow stimulus is delivered 3018 and control returns to block 3002, if not, inspiratory phase is reevaluated until it is not inspiratory 3007, 3017. If OSH criteria are not met 3014, the algorithm either stops 3019 or returns to 3002. It should be understood that certain logical steps can be combined or performed simultaneously. For example, the logical steps performed in blocks 3010 and 3012 may be combined such that a report of the occurrence of OSA in constitutes a signal to apply the stimulus appropriate for OSA, provided that the output of bock 3011 is positive.

A burst of electrical or mechanical stimulation is defined here as a temporally discrete occurrence of one (a single), or more (a series) of stimulus pulse(s), defined by a total duration from burst start to burst end of about 200 µsec to about 3 seconds. For electrical stimulation, individual stimulus pulses can have for example an amplitude of at least about 0.1 mA, and a duration of about 100 µsec to about 500 µsec, preferably about 200 µsec, presented as a single pulse, or multiple pulses. Two or more individual pulses can be presented, for example, at a frequency of at least about 20 Hz to about 40 Hz, preferably at about 30 Hz. For mechanical stimulation, a burst can comprise a series of one (a single) or more (a series) of mechanical stimulus pulses with a total duration from burst start to burst end of about 200 µsec to about 3 seconds. For mechanical stimulation, two or more individual stimulus pulses may be presented at a frequency of at least about 0.1 Hz to about 10 Hz, preferably about 0.33 Hz. It should be understood however that mechanical stimulation at a frequency approaching the physical limits of the physical apparatus may be faster than 10 Hz and can be used, particularly when pulses of small amplitude are being used. For mechanical stimulation, the characteristics of an individual stimulus pulse are determined by the nature of the mechanical stimulus being used. For example, a fluid mechanical stimulus pulse delivered to a mechanoreceptor in the skin or mucosa of the subject, would have a total volume determined by the flow rate multiplied by the duration of the stimulus pulse. In the case of fluid delivery, a fluid pulse may have a volume of about 0.5 ml to about 5 ml.

It should be appreciated that the steps represented by blocks 3006 and 3007 may be implemented sequentially or in parallel as input to block 3008, such that when the output of block 3008 is positive (apnea detected AND (respiratory phase =NOT inspiration) detected), block 3010 reports an occurrence of OSA and the swallow stimulus is applied 3012. For example, as shown in FIG. 6, a module implementing block 3006 may be configured with two separate outputs, one leading directly to block 3008, and a second one leading directly to block 3007, wherein the IRA and respiratory phase are provided separately to block 3008. Alternatively, a module implementing block 3006 may be configured with one output leading directly to block 3007, which is configured with an output directly to block 3008, wherein block 3007 is configured to provide both IRA and respiratory phase information to block 3008. It should also be understood that steps 3002-3018 may be performed once or multiple times as part of a reiterative process. Still further, it should be appreciated that the output of block 3007 may be alternatively positioned in the process, for example as an input directly to block 3010 and to block 3016, or to another block or blocks (not shown) in the process before the decision to apply a swallow stimulus, provided that a logical and function is performed on the IRA and the determination of respiratory phase, such that a swallow stimulus is applied only when IRA criteria are met and respiratory phase is not inspiratory.

When the output of block 3008, for example, is null, the process proceeds to the step in block 3014, to determine if conditions are such that the IRA criteria for OSH are currently met, generating a report of an occurrence of OSH 3016 and application of an OSH-specific swallow stimulus 3018.

FIG. 7 is a flow diagram of an alternative embodiment of process 3000, further including a determination whether CSA 3020 or CSH 3026 criteria are met, and if so, an occurrence of CSA 3022 or CSH 3028 is reported. Control proceeds to blocks 3023 and 3029, respectively which determine whether the subject is between inspiratory phases 3007, based on the previous respiratory pattern. If these conditions are met, this triggers application of a CSA-specific swallow stimulus 3024 or a CSH-specific swallow stimulus 3030. For central apneas or hypopnea, treatments alternative or in addition to swallow stimulation, such as phrenic nerve stimulation to elicit an inspiration are described in U.S. Pub. No. 2010/0125310. For phrenic nerve stimulation, the logic in blocks 3023 and 3029 would be reversed to ensure that respiratory phase is not expiratory before delivering stimulation designed to elicit inspiration. Steps represented by blocks 3002-3030 may performed once or multiple times as part of a reiterative process.

The produced stimulation signals may be square pulses or arbitrary waveforms, constant voltage, constant current, single stimuli or bursts of signal pulses. Stimulation location, amplitude, and/or waveform may be adjusted in a closed-loop based on current respiratory conditions such as respiratory phase, or based on conditions relayed by the apnea monitoring and detection module 1104 in response to previous stimulation. Stimulation waveforms may also contain features allowing for selective stimulation using current steering, directionally selective stimulation of efferent or afferent fibers, selectivity for stimulating axons of a particular diameter, or features designed to block transmission of undesired bioelectric activity.

In the methods, a swallow stimulus comprises an electrical or mechanical stimulus to a nerve, muscle, or sensory receptor in the subject that is sufficient to elicit all or part of the reflexive and pre-programmed coordinated activity of a swallow. For example, the swallow stimulus may comprise electrical stimulation to at least one swallow-related nerve, electrical stimulation to at least one swallow-related muscle, mechanical stimulation to at least one swallow-related sensory receptor in the skin or mucosa of the subject, or any combination thereof provided that the swallow stimulus is sufficient to elicit all or part of a swallow sequence in the subject. Stimulation of multiple targets may be delivered simultaneously, or in a sequence designed to elicit natural activation patterns in all or part of the 50 muscles normally involved in the swallow sequence. For electrical stimuli, the stimulus target may be an afferent nerve or an efferent nerve, and may include at least two swallow-related nerves wherein each swallow-related nerve is independently an afferent nerve or an efferent nerve. An afferent target is selected based on the ability of the afferent nerve, when stimulated, to elicit all or part of reflexive swallow pattern activity from the central nervous system of the subject. The target nerve can be, for example, the internal branch of the superior laryngeal nerve (iSLN), or the pharyngeal branch of the glossopharyngeal nerve. Alternatively or in addition, the swallow-related nerve can be an efferent nerve. An efferent target is selected based on the ability of the efferent nerve, when stimulated, to elicit motor activity in at least one effector in a swallow sequence, the motor activity comprising all or part of a swallow sequence in the subject. Mechanical stimulation may comprise stimulation to at least one swallow-related sensory receptor in the skin or mucosa of the subject, such as for example delivery of a liquid to at least one of the oral, nasal, or pharyngeal cavity of the subject that is sufficient to elicit all or part of a swallow sequence in a subject.

Still other applications of the invention will be apparent to those skilled in the art. For example, the device has the capacity to detect respiration rate, phase, and timing. This provides for general monitoring of vital signs, aside from apnea detection, and could provide respiration-related parameters to other devices such as external monitoring equipment, or implanted devices such as pacemakers or implantable defibrillators.

Further, apneas occurring during sleep or waking, as in cases of Cheyne-Stokes respiration or Charcot-Marie-Tooth disease can be effectively treated with the systems and methods described herein. Other adverse respiratory conditions, types of sleep disordered breathing, and dysphagia can be detected by monitoring naturally occurring receptors in the airway, such as narrowing or obstruction of the airway, snoring, presence of solids or fluids in the airway, respiratory difficulty in congestive heart failure, presence of reflux in the airway, or inappropriate magnitude or timing of airway muscle activity. Detection of these events might be applied to the detection and treatment of respiratory disorders such as asthma, dysphagia, aspiration pneumonia, or SIDS. Stimulation treatments could result in bronchodilation or bronchoconstriction, change in breathing pattern, swallow, cough, gag, muscle or sphincter activation or inhibition, change in mucus or other secretion, or other activity of the airway.

Accordingly, the methods also encompass a method for treating dysphagia, including a) sensing a dysphagia signal in a subject; b) detecting dysphagia based on the dysphagia signal; and (c) when dysphagia is detected, triggering the delivery of a swallow stimulus sufficient to elicit all or part of a swallow in the subject. These steps may be repeated to determine if a dysphagia signal persists following delivery of a swallow stimulus, and then to deliver another swallow stimulus in response. Swallow stimuli for treating dysphagia also include at least one of: electrical stimulation to at least one swallow-related nerve, electrical stimulation to at least one swallow-related muscle, and mechanical stimulation to at least one swallow-related sensory receptor in the skin or mucosa of the subject, and each of these may be delivered in a burst of simulation as described elsewhere herein. Electrical and mechanical stimuli include those as described herein above. Mechanical stimulation can include for example stimulation of at least one swallow-related sensory receptor in the skin or mucosa of the subject such as delivery of a liquid to at least one of the oral, nasal, or pharyngeal cavity of the subject. The method may further include a step comparable to sensing a respiratory signal 2002 in a subject, which signal is further indicative of respiratory phase in the subject over time, wherein the respiratory phase is an inspiratory phase, an expiratory phase or a zero flow phase. Delivery of a burst stimulus may be triggered to coincide with the expiratory phase or zero flow phase in the subject. Exemplary such methods thus include those in which burst stimulation is used, and further wherein the delivery of the burst stimulation is timed to coincide with the expiratory phase or zero flow phase of respiration in the subject, i.e., for delivery of the stimulus burst between inspiratory phases of the subject.

It is also to be understood that any of the methods or systems described herein may be selectively activated, for example when a subject is sleeping. The activation may be user initiated, optionally with a delay, according to a given schedule, by monitoring the heart rate of the subject, the orientation of the subject, etc.

Having now described the present disclosure in detail, examples will be more clearly understood by reference to the following examples of laboratory test procedures and methods which are included for purposes of illustration only and not intended to limit the scope of the present disclosure.

EXAMPLE 1

Delivery of Fluid Stimuli

Subjects are fitted with a nasal catheter and fully instrumented for polysomnography. The nasal catheter is a commercially available, Luer-lock, one-eyed, pediatric feeding tube with an outer 4 French diameter. The catheter is lubricated with a non-analgesic lubricant and advanced transnasally into the pharynx. The fluid delivery port of the catheter is positioned ~2 cm rostral to the upper esophageal sphincter (Dua et al., 2007) and oriented toward the posterior pharyngeal wall. Catheter position is verified laryngoscopically before being fixed in place using tape at the nostrils. A small diameter catheter is chosen to minimize possible increases in airway resistance which may influence swallowing patterns relative to respiration. A small catheter may also eliminate the need for analgesic lubricants, which have been shown to influence swallow function.

The optimal parameters for pharyngeal swallow stimulation in any given subject using fluid delivery are determined. Stimulus flow, volume, and timing are controlled in using a high accuracy peristaltic pump (Harvard Instruments, model 77). The pump is capable of flow rates from 0.01-750 ml/minute and can be controlled remotely using TTL logic. The pump is controlled using control logic from a digital signal processing workstation (Tucker-Davis Technologies RX5). To reduce acoustic and electrical noise, the pump and digital control unit are isolated in an adjacent room and connected to the nasal catheter by a length of tubing.

Inspiration is detected using an abdominal piezoelectric belt and used to control stimulation in real-time. Stimuli can be appropriately timed for delivery between breaths to elicit swallow during the between breath interval while maintaining normal respiratory drive. Stimulation begins shortly after the end of inspiration and is timed (based on respiration rate) to end before the onset of the subsequent inspiration.

EXAMPLE 2

Determination of Swallow Stimulus Thresholds

Swallow threshold measurements are carried out in awake subjects in the upright position. Subjects are fully instrumented for stimulation and recording, and stimulation is timed to occur in bursts between successive inspirations. All fluid stimuli consist of room-temperature, bottled "Sterile Water for Irrigation, USP" obtained from a medical supplier.

Thresholds are determined at a number of preselected flow rates. For each measurement, a flow rate is fixed and stimulus duration changed between successive stimuli until threshold is determined. The resulting stimulus volumes are calculated as flow X duration. Stimuli are delivered in discrete bursts between successive inspirations. Threshold events are defined as swallow, laryngeal reflex, or subject indication of discomfort. One goal of threshold measurements is to define the shortest duration/smallest volume that will reliably elicit swallow to single stimulus bursts. Another goal is to define stimuli that minimize the potential for discomfort, expulsive reflexes, or sensory arousal during sleep.

A minimum flow rate of 1 ml/minute is used. Additional flow rates are selected at increasing 2× intervals up to the limits of the equipment or subject acceptance. To obtain an upper estimate of acceptable flow rates, informal testing in adult humans has been performed, using water delivered orally through an 8 French catheter. Stimulation at a flow rate of ~5 ml/sec (~300 ml/minute) did not produce discomfort. Subject feedback is collected during the threshold measurement process and stimuli eliciting discomfort (e.g. at high flow rates or volumes) are eliminated from further testing.

Stimulus durations start at a minimum of 0.5 seconds and selected at increasing 0.5 second intervals to a maximum of 3.0 seconds. The maximum 3.0 second duration is estimated from normal waking respiration of 10-12 breaths/minute (5-6 second interval) (Dozier et al, 2006) and assuming a 50% duty cycle for inspiration. Preselected flow rates and durations result in the stimulus volumes shown in the table below. These volumes include the full range of threshold volumes reported for single swallows in previous studies (0.1 ml-2.0 ml) (Teramato et al., 1999; Jobin et al., 2007).

| Flow rate | | volume (ml) at selected durations (sec) | | | | | |
|---|---|---|---|---|---|---|---|
| ml per min | ml per sec | 0.5 sec | 1 sec | 1.5 sec | 2.0 sec | 2.5 sec | 3.0 sec |
| 1.00 | 0.02 | 0.01 | 0.02 | 0.03 | 0.04 | 0.05 | 0.06 |
| 2.00 | 0.03 | 0.02 | 0.03 | 0.05 | 0.07 | 0.08 | 0.10 |
| 4.00 | 0.07 | 0.03 | 0.07 | 0.10 | 0.13 | 0.17 | 0.20 |
| 8.00 | 0.13 | 0.07 | 0.13 | 0.20 | 0.27 | 0.33 | 0.40 |
| 16.00 | 0.27 | 0.13 | 0.27 | 0.40 | 0.53 | 0.67 | 0.80 |
| 32.00 | 0.53 | 0.27 | 0.53 | 0.80 | 1.07 | 1.33 | 1.60 |
| 64.00 | 1.07 | 0.53 | 1.07 | 1.60 | 2.13 | 2.67 | 3.20 |
| 128.00 | 2.13 | 1.07 | 2.13 | 3.20 | 4.27 | 5.33 | 6.40 |
| 256.00 | 4.27 | 2.13 | 4.27 | 6.40 | 8.53 | 10.67 | 12.80 |
| 512.00 | 8.53 | 4.27 | 8.53 | 12.80 | 17.07 | 21.33 | 25.60 |

Stimuli at low flow rates or volumes are not always sufficient to elicit a swallow to a single stimulus burst. Nonetheless, these sub-threshold stimuli deliver a bolus that remains in the pharynx until swallowed. To avoid any additive influence of preceding stimuli, the pharynx should be cleared by voluntary swallow or suction after each sub-threshold stimulus before a new stimulus can be delivered. This process is cumbersome and time consuming. As an alternative, an adaptive Bekesy-type threshold determination method is used, using a 1 up-1 down staircase to determine swallow threshold at each flow rate. The stimulus sequence begins at 0.5 sec, and stepped up between successive stimuli at 0.5 sec increments until a swallow or other threshold event occurred. At this "reversal point", stimulus duration is stepped down by 0.5 sec until no response is observed. This "staircase" process is repeated with the reversal points progressively bracketing the actual threshold. It is estimated that thresholds for 10 flow rates can be obtained using this method in less than 1 hour, resulting in a range of acceptable flow rates, stimulus durations, and volume thresholds.

After thresholds have been determined in the upright position, subjects assume a supine position and threshold stimuli are redelivered to the awake subject. Additional subject feedback is collected to determine which flow rates and volumes are most comfortable while supine and considered by the subject to be least likely arouse them during sleep.

EXAMPLE 3

Evaluation by Polysomnography

Polysomnographic recording methods, terminology, and scoring rules for sleep-related events are based on AASM guidelines (Iber et al., 2007). These are used to evaluate the effectiveness of a swallow stimulus for sleep apnea. All procedures are carried out by experienced sleep lab personnel. Acquired data includes EEG, EOG, submental EMG, ECG, thermistor-based nasal and oral airflow, nasal air pressure, pulse oximetry, respiratory inductance plethysmography at ribcage and abdomen, and body position.

The sleep EEG is derived by default from positions C3 and C4, using the contralateral mastoid (M1) as reference. Additional electrodes at F4 and $O_2$, also relative to M1, are recommended by AASM guidelines. The electrooculogram (EOG) are derived from electrodes at E1 (lower left canthus) and E2 (upper right canthus) relative to M2. Submental EMG is recorded using one electrode placed at midline above the chin and 2 lateral electrodes placed below the chin. The subject is monitored at all times by experienced sleep laboratory personnel.

Sleep, respiratory, and swallow related variables are acquired across all subjects and treatments.

Sleep Architecture Per Session:
  1. Recording time
  2. Total sleep time (TST)
  3. Sleep efficiency
  4. Sleep latency
  5. REM latency
  6. Wake latency
  7. Number of arousals
  8. Number of stage 0 (wake) periods
  9. % Stage 1 sleep
  10. % Stage 2 sleep
  11. % Stage 3 and/or 4 sleep (SWS)
  12. % REM sleep
  13. Number of REM periods Cardiorespiratory Variables Per Session:
  1. AHI
  2. Apnea Index
  3. Hypopnea Index
  4. Duration of apnea/hypopnea
  5. Mean, minimum, and maximum oxygen saturation
  6. Mean, minimum, and maximum respiration rate
  7. Mean, minimum, and maximum heart rate
  8. Mean saturation change in apnea/hypopnea
  9. Number of desaturations >4%
  10. Number of desaturations >10%
  11. Length of desaturations >4%
  12. Length of desaturations >10%
  13. % apnea/hypopnea (duration/TST)
  14. Arousal index (n per hour TST)
  15. Swallow index (n per hour TST)
  16. Expiratory reflex index (n per hour TST)

Event-by-Event (Stimulus-Related) Variables:
  1. Swallow reflex, as indicated by submental EMG, airflow, video, and respiratory inductance plethysmography.
  2. Expiratory reflex (e.g. expiration, cough, sneeze) as indicated by submental EMG, airflow, video, and respiratory inductance plethysmography.
  3. Apnea, including respiratory effort, SpO2, and airflow.
  4. Arousals, as indicated by increased respiratory rate, increased heart rate, or lighter sleep stage as measured by polysomnography.

Event-by-event analysis is comparable to that used by Page and Jeffrey (1998). Each stimulus is classified according to the sleep stage in the 1 minute epoch immediately prior to delivery. The epoch immediately before the stimulus serves as a control and the epoch immediately after as a treatment period for each stimulus. The effect of stimulation is made by comparing events in these epochs. For example, respiratory rate, heart rate, SpO2 are averaged for the control period and treatment periods and quantified as % change.

Categorical events observed in the treatment period, such as swallow, arousal, or expiratory reflex are expressed as % of total number of stimuli. The effect of treatment group and sleep state on occurrence of categorical events in the treatment period is determined using $\chi^2$ test. The effect of treatment group and sleep state on categorical events in the control period is determined in the same manner.

It will be readily apparent to those skilled in the art that other suitable modifications and adaptations of the methods of the present disclosure described herein are obvious and may be made using suitable equivalents without departing from the scope of the present disclosure or the embodiments disclosed herein. The disclosures of all journal references, U.S. patents and publications referred to herein are hereby incorporated by reference in their entireties.

REFERENCES

Dozier T S, Brodsky M B, Michel Y, Walters B C Jr, Martin-Harris B. (2006) Coordination of swallowing and respiration in normal sequential cup swallows. LARYNGOSCOPE. 2006 AUG; 116(8): 1489-93.

Dua K S, Bajaj J S, Rittmann T, Hofmann C, Shaker R. (2007) Safety and feasibility of evaluating airway-protective reflexes during sleep: new technique and preliminary results. GASTROINTEST ENDOSC. MAR; 65(3):483-6.

Iber C, Ancoli-Israel S, Chesson A, Quan S F (2007) EDITORS. The AASM manual for the scoring of sleep and associated events: rules, terminology, and technical specification. 1ST ED. WESTCHESTER, IL: AMERICAN ACADEMY OF SLEEP MEDICINE; 2007.

Jobin V, Champagne V, Beauregard J, Charbonneau I, McFarland D H, Kimoff R J. (2007) Swallowing function and upper airway sensation in obstructive sleep apnea. J APPL PHYSIOL. 2007 APR; 102(4): 1587-94.

Page M, Jeffery H E. (1998) Airway protection in sleeping infants in response to pharyngeal fluid stimulation in the supine position. PEDIATR RES. NOV; 44(5):691-8.

Teramoto S, SUDO E, MATSUSE T, OHGA E, ISHII T, OUCHI Y, FUKUCHI Y. (1999) Impaired swallowing reflex in subjects with obstructive sleep apnea syndrome. CHEST. 1999 JUL; 116(1):17-21.

Weaver, T. E. and Grunstein, R. R. (2008) "Adherence to Continuous Positive Airway Pressure Therapy: The Challenge to Effective Treatment", Proc Am Thorac Soc Vol 5. pp 173-178.

What is claimed is:

1. A system for treating apnea in a subject, comprising:
   a) an electrode configured for positioning in contact with the internal branch of the superior laryngeal nerve (iSLN) of the subject;
   b) a control unit comprising:
      i. a signal conditioning module for conditioning an electroneurogram signal from the electrode;
      ii. an apnea monitoring and detection module operatively coupled to the signal conditioning module and configured for computing an index of respiratory activity from the conditioned electroneurogram signal, wherein when the index of respiratory activity is at or above a predetermined level, the index of respiratory activity is indicative of an occurrence of an apneic event; and
      iii. a therapy control module operatively coupled to the apnea monitoring and detection module and configured to control delivery of a swallow stimulus to the subject when the index of respiratory activity is indicative of an occurrence of an apneic event.

2. The system of claim 1, wherein the swallow stimulus is at least one of: electrical stimulation to at least one swallow-related nerve, electrical stimulation to at least one swallow-related muscle, and mechanical stimulation to at least one swallow-related sensory receptor.

3. The system of claim 1, wherein the swallow stimulus comprises a burst of electrical stimulation or a burst of mechanical stimulation.

4. The system of claim 2, wherein the swallow stimulus comprises mechanical stimulation to at least one swallow-related sensory receptor comprising delivery of a liquid to at least one of the oral, nasal, or pharyngeal cavity of the subject.

5. The system of claim 2, further comprising:
   a) a stimulation module operatively connected to the therapy control module; and
   b) a stimulation output device coupled to the stimulation module and configured for delivery of the swallow stimulus to the subject, wherein the stimulation module is configured to generate the swallow stimulus through the stimulation output device.

6. The system of claim 5, wherein the stimulation output device comprises a stimulation electrode coupled to the stimulation module and configured for positioning in contact with at least one swallow-related nerve or muscle, wherein the stimulation module is configured to generate electrical stimulation through the stimulation electrode to at least one swallow-related nerve or muscle.

7. The system of claim 6, wherein the therapy control module is configured to activate bursts of electrical stimulation to at least one swallow-related nerve or muscle.

8. The system of claim 5, wherein the stimulation output device comprises a mechanical stimulation delivery device configured to generate mechanical stimulation and deliver the stimulation to at least one swallow-related sensory receptor in the skin or mucosa of the subject.

9. The system of claim 8, wherein the mechanical stimulation delivery device is configured for delivery of a liquid to the oral, nasal, or pharyngeal cavity of the subject.

10. The system of claim 9, wherein the therapy control module is configured to activate bursts of mechanical stimulation to the subject.

11. The system of any of any of claims 1-3, wherein the apnea monitoring and detection module is further configured to detect an apnea.

12. The system of any of claims 1-3, wherein the index of respiratory activity is indicative of at least one of upper airway pressure, airway stretch, and airway temperature.

13. The system of claim any of claim 12, wherein the index of respiratory activity is indicative of upper airway pressure.

14. The system of any of claims 1-3, wherein the index of respiratory activity is further indicative of the respiratory phase in the subject over time, wherein the respiratory phase comprises at least one of an inspiratory phase, an expiratory phase and a zero flow phase.

15. The system of claim 14, wherein the index of respiratory activity is indicative of respiratory phase, and the therapy control module is further configured to synchronize delivery of burst mechanical stimulation, to at least one swallow-related sensory receptor in the skin or mucosa of the subject between inspiratory phases of the subject, the burst stimulation sufficient to elicit sufficient to elicit all or part of a swallow sequence in the subject.

16. The system of claim 14, wherein the index of respiratory activity is indicative of respiratory phase, and the therapy control module is further configured to synchronize delivery of burst electrical stimulation, to at least one swallow-related muscle between inspiratory phases of the subject, the burst stimulation sufficient to elicit sufficient to elicit all or part of a swallow sequence in the subject.

17. The system of claim 14, wherein the index of respiratory activity is indicative of respiratory phase, and the therapy control module is further configured to synchronize delivery of burst electrical stimulation to at least one swallow-related nerve between inspiratory phases, the burst stimulation sufficient to elicit sufficient to elicit all or part of a swallow sequence in the subject.

18. The system of claim 17, wherein the swallow-related nerve is an afferent nerve or an efferent nerve.

19. The system of claim 17, wherein the swallow-related nerve is an afferent nerve, wherein stimulation of the afferent nerve triggers swallow reflexive pattern activity in the central nervous system of the subject that is sufficient to elicit all or part of a swallow sequence by the subject.

20. The system of claim 2, wherein the swallow-related nerve is the superior laryngeal nerve (SLN).

21. The system of claim 2, wherein the swallow-related nerve the internal branch of the superior laryngeal nerve.

22. The system of claim 2, wherein the swallow-related nerve is the glossopharyngeal nerve.

23. The system of claim 2, wherein the swallow-related nerve is the pharyngeal branch of the glossopharyngeal nerve.

24. The system of claim 2, wherein the swallow-related nerve is an efferent nerve, wherein stimulation of the efferent nerve elicits motor activity in at least one effector of a swallow response in the subject, the motor activity comprising all or part of a swallow sequence by the subject.

25. The system of claim 3, wherein the apnea monitoring and detection module is further configured to compare the index of respiratory activity following delivery of each burst of stimulation, to a predetermined recovery threshold and thereby detect recovery from apnea in response to each burst of stimulation.

26. The system of claim 25, wherein the therapy control module is further configured to repeat delivery of burst stimulation when recovery from apnea is not detected.

27. The system of any of claims 1-10, wherein the system is partially or fully implantable.

28. A method for treating apnea, the method comprising:
a) sensing a respiratory signal in a subject;
b) detecting apnea based on the respiratory signal;
c) when apnea is detected, triggering the delivery of a swallow stimulus sufficient to elicit all or part of a swallow in the subject; and
d) optionally repeating steps (a) through (c).

29. The method of claim 28, wherein the swallow stimulus comprises at least one of: electrical stimulation to at least one swallow-related nerve, electrical stimulation to at least one swallow-related muscle, and mechanical stimulation to at least one swallow-related sensory receptor in the skin or mucosa of the subject, the swallow stimulus sufficient to elicit all or part of a swallow sequence in the subject.

30. The method of claim 29, wherein the swallow stimulus comprises burst electrical stimulation or burst mechanical stimulation.

31. The method of claim 29, wherein the swallow stimulus comprises mechanical stimulation to at least one swallow-related sensory receptor, comprising delivery of a liquid to at least one of the oral, nasal, or pharyngeal cavity of the subject.

32. The method of claim 29, wherein the swallow stimulus comprises electrical stimulation to at least one swallow-related nerve or muscle.

33. The method of claim 30, wherein the respiratory signal further comprises a signal indicative of respiratory phase in the subject over time, wherein the respiratory phase comprises at least one of an inspiratory phase, an expiratory phase and a zero flow phase.

34. The method of claim 33, wherein the triggering of the electrical burst stimulation or mechanical burst stimulation comprises synchronizing the delivery of the burst stimulation between inspiratory phases of the subject.

35. The method of claim 28, further comprising computing an index of respiratory activity indicative of at least one of upper airway pressure, airway stretch, and airway temperature.

36. The method of claim 35, wherein the index of respiratory activity is indicative of upper airway pressure.

37. A method for treating sleep apnea, the method comprising:
a) recording an electroneurogram signal from the internal branch of the superior laryngeal nerve (iSLN) of the subject;
b) conditioning the electroneurogram signal;
c) computing an index of respiratory activity from the conditioned electroneurogram signal;
d) reporting an occurrence of an apneic event when the index of respiratory activity is at or above a predetermined level; and
e) upon occurrence of an apneic event, triggering delivery of a swallow stimulus to the subject, wherein the swallow stimulus is sufficient to elicit all or part of a swallow sequence in the subject.

38. The method of claim 37, wherein the swallow stimulus comprises at least one of: electrical stimulation to at least one swallow-related nerve, electrical stimulation to at least one swallow-related muscle, and mechanical stimulation to at least one swallow-related sensory receptor in the skin or mucosa of the subject.

39. The method of claim 38, wherein the swallow stimulus comprises burst electrical stimulation or burst mechanical stimulation.

40. The method of claim 38, wherein the swallow stimulus comprises mechanical stimulation to at least one swallow-related sensory receptor, comprising delivery of a liquid to at least one of the oral, nasal, or pharyngeal cavity of the subject.

41. The method of claim 38, wherein the swallow stimulus comprises electrical stimulation to at least one swallow-related swallow-related nerve or muscle.

42. The method of claim 41, comprising electrical stimulation to at least two swallow-related nerves, at least two swallow-related muscles, or at least a swallow-related nerve and a swallow-related muscle.

43. The method of claim 39, wherein the respiratory signal further comprises a signal indicative of respiratory phase in the subject over time, wherein the respiratory phase comprises at least one of an inspiratory phase, an expiratory phase and a zero flow phase.

44. The method of claim 43, wherein the respiratory signal is indicative of respiratory phase in the subject over time, and the triggering of the electrical burst stimulation or mechanical burst stimulation comprises synchronizing the delivery of the burst stimulation between inspiratory phases of the subject.

45. The method of claim 39, wherein the index of respiratory activity is indicative of at least one of upper airway pressure, airway stretch, and airway temperature.

46. The method of claim 45, wherein the index of respiratory activity is indicative of upper airway pressure.

47. The method of claim 43, wherein the swallow stimulus comprises burst electrical stimulation to at least one swallow-related nerve wherein a swallow-related nerve is an afferent nerve or an efferent nerve.

48. The method of claim 47, comprising burst electrical stimulation to at least two swallow-related nerves wherein each swallow-related nerve is independently an afferent nerve or an efferent nerve.

49. The method of claim 41, wherein the swallow-related nerve is an afferent nerve, wherein stimulation of the afferent nerve elicits swallow reflexive pattern activity from the central nervous system of the subject sufficient to elicit all or part of a swallow sequence in the subject.

50. The method of claim 38, wherein the swallow-related nerve is the internal branch of the superior laryngeal nerve (iSLN).

51. The method of claim 38, wherein the swallow-related nerve is the pharyngeal branch of the glossopharyngeal nerve.

52. The method of claim 38, wherein the swallow-related nerve is an efferent nerve, wherein stimulation of the efferent nerve elicits motor activity in at least one effector in a swallow sequence, the motor activity comprising all or part of a swallow sequence in the subject.

53. The method of any of claims 39-52, further comprising comparing the electroneurogram signal following delivery of each burst of stimulation, to a predetermined recovery threshold and thereby detecting recovery from apnea in response to each burst of stimulation.

54. The method of claim 53, further comprising repeating a burst of stimulation when recovery from apnea is not detected.

55. The method of any of claims 39 and 41-53, wherein delivering electrical stimulation comprises delivering a burst of stimulus pulses having a frequency of at least about 20 Hz to about 40 Hz, wherein each pulse has an amplitude of greater than about 0.1 mA and a duration of about 200 μsec.

56. A device for treating apnea in a subject, comprising:
a) an electrode configured for positioning in contact with the internal branch of the superior laryngeal nerve (iSLN) of the subject, further configured for obtaining an electroneurogram signal from the iSLN and for delivering electrical stimulation to the iSLN;

b) a control unit comprising:
  i. a signal conditioning module for conditioning the electroneurogram signal from the electrode; and
  ii. an apnea monitoring and detection module operatively coupled to the signal conditioning module and configured for computing an index of respiratory activity from the conditioned electroneurogram signal, wherein when the index of respiratory activity is at or above a predetermined level, the index of respiratory activity is indicative of an occurrence of an apneic event;
  iii. a therapy control module wherein the therapy control module is configured to control delivery of a swallow stimulus, wherein delivery of the swallow stimulus is triggered when the index of respiratory activity is indicative of an occurrence of an apneic event.

57. The device of claim 56, wherein the therapy control module is configured to control delivery of electrical stimulation through the electrode to at least one swallow-related nerve when the index of respiratory activity is indicative of an occurrence of an apneic event.

58. The device of claim 56, wherein the control unit comprises a respiratory phase module configured to determine respiratory phase from the index of respiratory activity and to generate a respiratory phase signal from the subject.

59. The device of claim 58, wherein the therapy control module is further configured to activate burst stimulation of the iSLN between inspiratory phases based on the respiratory phase signal, the burst stimulation sufficient to produce all or part of a swallow sequence in the subject.

60. The device of claim 59, wherein the electrode and therapy control module are implantable.

61. The device of claim 56 further comprising a stimulus output device configured for oral, nasal or pharyngeal delivery of a liquid to the subject and operatively coupled to the therapy control module, wherein the therapy control module is further configured to activate oral, nasal or pharyngeal delivery of liquid to the subject when the index of respiratory activity is indicative of an occurrence of an apneic event.

62. A method for treating dysphagia, the method comprising:
  a) sensing a dysphagia signal in a subject;
  b) detecting dysphagia based on the dysphagia signal;
  c) when dysphagia is detected, triggering the delivery of a swallow stimulus sufficient to elicit all or part of a swallow in the subject; and
  d) optionally repeating steps (a)-(c).

63. The method of claim 62, wherein the swallow stimulus comprises at least one of: electrical stimulation to at least one swallow-related nerve, electrical stimulation to at least one swallow-related muscle, and mechanical stimulation to at least one swallow-related sensory receptor in the skin or mucosa of the subject.

64. The method of claim 62, wherein the swallow stimulus comprises burst electrical stimulation or burst mechanical stimulation.

65. The method of claim 62, further comprising sensing a respiratory signal, wherein the respiratory signal is indicative of respiratory phase, wherein the respiratory phase is either an inspiratory phase, an expiratory phase, or a zero flow phase and the triggering of the burst stimulation comprises synchronizing the delivery of the burst stimulation between inspiratory phases of the subject.

66. The method of claim 62, wherein the swallow stimulus comprises mechanical stimulation to at least one swallow-related sensory receptor, comprising delivery of a liquid to at least one of the oral, nasal, or pharyngeal cavity of the subject.

67. The method of claim 62, wherein the swallow stimulus comprises electrical stimulation to at least one swallow-related nerve or muscle.

* * * * *